US009089636B2

(12) United States Patent
Gonnelli

(10) Patent No.: US 9,089,636 B2
(45) Date of Patent: *Jul. 28, 2015

(54) METHODS AND DEVICES FOR DELIVERING GLP-1 AND USES THEREOF

(75) Inventor: Robert R. Gonnelli, Mahwah, NJ (US)

(73) Assignee: VALERITAS, INC., Parsippany, NJ (US)

( * ) Notice: Subject to any disclaimer, the term of this patent is extended or adjusted under 35 U.S.C. 154(b) by 544 days.

This patent is subject to a terminal disclaimer.

(21) Appl. No.: 11/175,990

(22) Filed: Jul. 5, 2005

(65) Prior Publication Data

US 2006/0030838 A1     Feb. 9, 2006

Related U.S. Application Data

(60) Provisional application No. 60/585,330, filed on Jul. 2, 2004.

(51) Int. Cl.
*A61K 9/22*     (2006.01)
*A61M 5/142*     (2006.01)
*A61K 38/26*     (2006.01)
(Continued)

(52) U.S. Cl.
CPC ............ *A61M 5/14248* (2013.01); *A61K 38/26* (2013.01); *A61M 5/148* (2013.01); *A61M 5/1452* (2013.01); *A61K 38/00* (2013.01); *A61M 5/14593* (2013.01); *A61M 5/155* (2013.01); *A61M 2005/14506* (2013.01); *A61M 2005/14513* (2013.01)

(58) Field of Classification Search
CPC ............... A61M 2005/14513; A61M 5/14276; A61M 2005/14506; A61M 2230/04; A61M 5/148; A61M 5/16809; A61M 5/14248; A61M 38/26; A61M 5/1452
USPC .............. 604/890.1, 891.1; 514/12, 2; 417/22
See application file for complete search history.

(56) References Cited

U.S. PATENT DOCUMENTS 2,828,743 A     4/1858     Ashkenaz et al.
2,605,765 A     8/1952     Kollsman
(Continued)

FOREIGN PATENT DOCUMENTS

DE     3634725 A1     4/1988
DE     3739657 A1     5/1988
(Continued)

OTHER PUBLICATIONS

Banks et al., Brain uptake of the glucagon-like peptide-1 antagonist exendin(9-39) after intranasal administration. J Pharmacol Exp Ther. 309(2): 469-75, 2004.
(Continued)

*Primary Examiner* — Aarti B Berdichevsky
*Assistant Examiner* — Bradley Osinski
(74) *Attorney, Agent, or Firm* — Morgan, Lewis & Bockius LLP

(57) ABSTRACT

The invention provides various devices for delivering Glucagon-Like Peptide-1 (7-36), in various infusion patterns and rates, to optimally stimulate carbohydrate metabolism, to inhibit gastropancreatic secretion and gastric motility, and to treat various disease conditions (including diabete) as described in the instant specification. The devices and methods of the invention provide various ways to deliver doses (escalating, constant, on demand, etc.) of GLP-1 in response to different patient need.

26 Claims, 9 Drawing Sheets

(51) Int. Cl.
  *A61M 5/145* (2006.01)
  *A61M 5/148* (2006.01)
  *A61M 5/155* (2006.01)
  *A61K 38/00* (2006.01)

(56) References Cited

U.S. PATENT DOCUMENTS

| | | |
|---|---|---|
| 2,702,547 A | 2/1955 | Glass |
| 3,055,362 A | 9/1962 | Uytenbogaart |
| 3,187,749 A | 6/1965 | Sarnoff |
| 3,731,681 A | 5/1973 | Blackshear et al. |
| 3,886,938 A | 6/1975 | Szabo et al. |
| 3,963,151 A | 6/1976 | North, Jr. |
| 4,042,153 A | 8/1977 | Callahan et al. |
| 4,065,230 A | 12/1977 | Gezari |
| 4,085,749 A | 4/1978 | Chambron |
| 4,150,672 A | 4/1979 | Whitney et al. |
| 4,190,048 A | 2/1980 | Sampson |
| 4,193,397 A | 3/1980 | Tucker et al. |
| 4,202,333 A | 5/1980 | Thill et al. |
| 4,209,014 A | 6/1980 | Sefton |
| 4,258,711 A | 3/1981 | Tucker et al. |
| 4,265,241 A | 5/1981 | Portner et al. |
| 4,267,836 A | 5/1981 | Whitney et al. |
| 4,298,000 A | 11/1981 | Thill et al. |
| 4,313,439 A | 2/1982 | Babb et al. |
| 4,340,048 A | 7/1982 | Eckenhoff |
| 4,351,335 A | 9/1982 | Whitney et al. |
| 4,360,019 A | 11/1982 | Portner et al. |
| 4,398,908 A | 8/1983 | Siposs |
| 4,411,651 A | 10/1983 | Schulman |
| 4,430,079 A | 2/1984 | Thill et al. |
| 4,431,426 A | 2/1984 | Groshong et al. |
| 4,437,859 A | 3/1984 | Whitehouse et al. |
| 4,443,218 A * | 4/1984 | DeCant et al. ............... 604/67 |
| 4,496,343 A | 1/1985 | Prosl et al. |
| 4,498,843 A * | 2/1985 | Schneider et al. ............ 417/22 |
| 4,525,165 A | 6/1985 | Fischell |
| 4,529,401 A | 7/1985 | Leslie et al. |
| 4,548,607 A | 10/1985 | Harris |
| 4,552,561 A | 11/1985 | Eckenhoff et al. |
| 4,559,038 A | 12/1985 | Berg et al. |
| 4,561,856 A | 12/1985 | Cochran |
| 4,565,542 A | 1/1986 | Berg |
| 4,568,335 A | 2/1986 | Updike et al. |
| 4,583,973 A | 4/1986 | Humphrey et al. |
| 4,596,575 A | 6/1986 | Rosenberg et al. |
| 4,601,707 A | 7/1986 | Albisser et al. |
| H150 H * | 11/1986 | Hankner et al. ........... 604/890.1 |
| 4,627,839 A | 12/1986 | Young |
| 4,648,872 A | 3/1987 | Kamen |
| 4,650,469 A | 3/1987 | Berg et al. |
| 4,685,902 A | 8/1987 | Edwards et al. |
| 4,699,615 A | 10/1987 | Fischell et al. |
| 4,715,852 A | 12/1987 | Reinicke et al. |
| 4,718,893 A | 1/1988 | Dorman et al. |
| 4,723,947 A | 2/1988 | Konopka |
| 4,731,058 A | 3/1988 | Doan |
| 4,734,092 A | 3/1988 | Millerd |
| 4,741,736 A | 5/1988 | Brown |
| 4,744,786 A | 5/1988 | Hooven |
| 4,747,824 A | 5/1988 | Spinello |
| 4,749,109 A | 6/1988 | Kamen |
| 4,755,172 A | 7/1988 | Baldwin |
| 4,772,263 A | 9/1988 | Dorman et al. |
| 4,772,273 A | 9/1988 | Alchas |
| 4,781,688 A | 11/1988 | Thoma et al. |
| 4,784,576 A | 11/1988 | Bloom et al. |
| 4,784,577 A | 11/1988 | Ritson et al. |
| 4,790,829 A | 12/1988 | Bowden et al. |
| 4,808,161 A | 2/1989 | Kamen |
| 4,808,167 A | 2/1989 | Mann et al. |
| 4,813,951 A | 3/1989 | Cannon et al. |
| 4,816,019 A | 3/1989 | Kamen |
| 4,818,186 A | 4/1989 | Pastrone et al. |
| 4,822,339 A | 4/1989 | Tran |
| 4,826,482 A | 5/1989 | Kamen |
| 4,834,704 A | 5/1989 | Reinicke |
| 4,838,857 A | 6/1989 | Strowe et al. |
| 4,842,584 A | 6/1989 | Pastrone |
| 4,846,806 A | 7/1989 | Wigness et al. |
| 4,856,340 A | 8/1989 | Garrison |
| 4,861,341 A | 8/1989 | Woodburn |
| 4,874,386 A | 10/1989 | O'Boyle |
| 4,886,499 A | 12/1989 | Cirelli et al. |
| 4,894,054 A | 1/1990 | Miskinyar |
| 4,900,305 A | 2/1990 | Smith et al. |
| 4,902,278 A | 2/1990 | Maget et al. |
| 4,919,134 A | 4/1990 | Streeter |
| 4,925,444 A | 5/1990 | Orkin et al. |
| 4,927,411 A | 5/1990 | Pastrone et al. |
| 4,931,050 A | 6/1990 | Idriss |
| 4,952,210 A | 8/1990 | Alchas |
| 4,971,900 A | 11/1990 | Ahnell et al. |
| 4,976,162 A | 12/1990 | Kamen |
| 4,976,696 A | 12/1990 | Sanderson et al. |
| 4,998,926 A | 3/1991 | Alchas |
| 5,000,994 A | 3/1991 | Romberg et al. |
| 5,009,641 A | 4/1991 | Gorton |
| 5,024,664 A | 6/1991 | Mitchell |
| 5,037,396 A | 8/1991 | Streeter |
| 5,039,279 A | 8/1991 | Natwick et al. |
| 5,041,094 A | 8/1991 | Perego et al. |
| 5,045,064 A | 9/1991 | Idriss |
| 5,053,031 A | 10/1991 | Borsanyi |
| 5,055,001 A | 10/1991 | Natwick et al. |
| 5,059,174 A | 10/1991 | Vaillancourt |
| 5,062,774 A | 11/1991 | Kramer et al. |
| 5,088,515 A | 2/1992 | Kamen |
| 5,090,963 A | 2/1992 | Gross et al. |
| 5,098,262 A | 3/1992 | Wecker et al. |
| 5,100,380 A | 3/1992 | Epstein et al. |
| 5,106,374 A | 4/1992 | Apperson et al. |
| 5,106,627 A * | 4/1992 | Aebischer et al. ............ 424/424 |
| 5,108,367 A | 4/1992 | Epstein et al. |
| 5,135,498 A | 8/1992 | Kam et al. |
| 5,135,500 A | 8/1992 | Zdeb |
| 5,144,515 A | 9/1992 | Frauhauf et al. |
| 5,158,437 A | 10/1992 | Natwick et al. |
| 5,165,869 A * | 11/1992 | Reynolds ...................... 417/385 |
| 5,167,631 A | 12/1992 | Thompson et al. |
| 5,169,390 A | 12/1992 | Athayde et al. |
| 5,176,502 A | 1/1993 | Sanderson et al. |
| 5,176,641 A | 1/1993 | Idriss |
| 5,176,644 A | 1/1993 | Srisathapat et al. |
| 5,178,182 A | 1/1993 | Kamen |
| 5,178,609 A | 1/1993 | Ishikawa |
| 5,180,287 A | 1/1993 | Natwick et al. |
| 5,181,910 A | 1/1993 | Scanlon |
| 5,188,603 A | 2/1993 | Vaillancourt |
| 5,193,990 A | 3/1993 | Kamen et al. |
| 5,197,322 A | 3/1993 | Indravudh |
| 5,207,642 A | 5/1993 | Orkin et al. |
| 5,207,666 A | 5/1993 | Idriss et al. |
| 5,211,201 A | 5/1993 | Kamen et al. |
| 5,217,442 A | 6/1993 | Davis |
| 5,219,279 A | 6/1993 | Natwick et al. |
| 5,219,428 A | 6/1993 | Stern |
| 5,222,946 A | 6/1993 | Kamen |
| 5,232,449 A | 8/1993 | Stern et al. |
| 5,242,408 A | 9/1993 | Jhuboo et al. |
| 5,248,300 A | 9/1993 | Bryant et al. |
| 5,250,649 A | 10/1993 | Onwumere et al. |
| 5,254,096 A | 10/1993 | Rondelet et al. |
| 5,257,971 A | 11/1993 | Lord et al. |
| 5,257,987 A | 11/1993 | Athayde et al. |
| 5,259,732 A | 11/1993 | Stern |
| 5,261,884 A | 11/1993 | Stern et al. |
| 5,263,323 A | 11/1993 | Maus et al. |
| 5,281,210 A | 1/1994 | Burke et al. |
| 5,290,240 A | 3/1994 | Horres, Jr. |
| 5,295,966 A | 3/1994 | Stern et al. |
| 5,295,967 A | 3/1994 | Rondelet et al. |
| 5,300,041 A | 4/1994 | Haber et al. |

(56) References Cited

U.S. PATENT DOCUMENTS

| | | |
|---|---|---|
| 5,304,126 A | 4/1994 | Epstein et al. |
| 5,306,257 A | 4/1994 | Zdeb |
| 5,308,334 A | 5/1994 | Sancoff |
| 5,312,364 A | 5/1994 | Jacobs et al. |
| 5,318,540 A | 6/1994 | Athayde et al. |
| 5,319,979 A | 6/1994 | Abrahamson |
| 5,320,600 A | 6/1994 | Lambert |
| 5,322,422 A | 6/1994 | Natwick et al. |
| 5,328,459 A | 7/1994 | Laghi |
| 5,338,157 A | 8/1994 | Blomquist |
| 5,338,312 A | 8/1994 | Montgomery |
| 5,349,852 A | 9/1994 | Kamen et al. |
| 5,350,357 A | 9/1994 | Kamen et al. |
| 5,356,379 A | 10/1994 | Vaillancourt |
| 5,364,242 A | 11/1994 | Olsen |
| 5,368,562 A | 11/1994 | Blomquist et al. |
| 5,368,571 A | 11/1994 | Horres, Jr. |
| 5,370,622 A | 12/1994 | Livingston et al. |
| 5,376,070 A | 12/1994 | Purvis et al. |
| 5,389,078 A | 2/1995 | Zalesky et al. |
| 2,703,084 A | 3/1995 | Tomlinson |
| 5,396,925 A | 3/1995 | Poli |
| 5,399,166 A | 3/1995 | Laing |
| 5,399,823 A | 3/1995 | McCusker |
| 5,405,614 A | 4/1995 | D'Angelo et al. |
| 5,421,823 A | 6/1995 | Kamen et al. |
| 5,431,626 A | 7/1995 | Bryant et al. |
| 5,431,634 A | 7/1995 | Brown |
| 5,433,710 A | 7/1995 | VanAntwerp et al. |
| 5,438,510 A | 8/1995 | Bryant et al. |
| 5,445,621 A | 8/1995 | Poli et al. |
| 5,447,286 A | 9/1995 | Kamen et al. |
| 5,453,099 A | 9/1995 | Lee et al. |
| 5,456,909 A | 10/1995 | Marsh, Jr. et al. |
| 5,456,940 A | 10/1995 | Funderburk |
| 5,460,618 A | 10/1995 | Harreld |
| 5,462,525 A | 10/1995 | Srisathapat et al. |
| 5,464,392 A | 11/1995 | Epstein et al. |
| 5,466,218 A | 11/1995 | Srisathapat et al. |
| 5,472,317 A | 12/1995 | Field et al. |
| 5,474,683 A | 12/1995 | Bryant et al. |
| 5,480,386 A | 1/1996 | Brohy et al. |
| 5,485,408 A | 1/1996 | Blomquist |
| 5,487,737 A | 1/1996 | Meyer et al. |
| 5,492,534 A | 2/1996 | Athayde et al. |
| 5,505,706 A | 4/1996 | Maus et al. |
| 5,505,709 A | 4/1996 | Funderburk et al. |
| 5,505,713 A | 4/1996 | Van Antwerp |
| 5,507,277 A | 4/1996 | Rubsamen et al. |
| 5,514,103 A | 5/1996 | Srisathapat et al. |
| 5,515,713 A | 5/1996 | Saugues et al. |
| 5,526,844 A | 6/1996 | Kamen et al. |
| 5,527,288 A | 6/1996 | Gross et al. |
| 5,527,307 A | 6/1996 | Srisathapat et al. |
| 5,529,463 A | 6/1996 | Layer et al. |
| 5,531,697 A | 7/1996 | Olsen et al. |
| 5,531,698 A | 7/1996 | Olsen |
| 5,533,389 A | 7/1996 | Kamen et al. |
| 5,533,994 A | 7/1996 | Meyer et al. |
| 5,538,399 A | 7/1996 | Johnson |
| 5,538,511 A | 7/1996 | Van Antwerp |
| 5,540,561 A | 7/1996 | Johnson |
| 5,544,519 A | 8/1996 | Hammarberg et al. |
| 5,545,152 A | 8/1996 | Funderburk et al. |
| 5,564,915 A | 10/1996 | Johnson |
| 5,567,119 A | 10/1996 | Johnson |
| 5,567,136 A | 10/1996 | Johnson |
| 5,569,186 A | 10/1996 | Lord et al. |
| 5,570,716 A | 11/1996 | Kamen et al. |
| 5,574,008 A | 11/1996 | Johnson et al. |
| 5,575,310 A | 11/1996 | Kamen et al. |
| 5,575,770 A | 11/1996 | Melsky et al. |
| 5,578,002 A | 11/1996 | Slettenmark et al. |
| 5,578,005 A | 11/1996 | Sancoff et al. |
| 5,578,012 A | 11/1996 | Kamen et al. |
| 5,582,591 A | 12/1996 | Cheikh et al. |
| 5,584,813 A | 12/1996 | Livingston et al. |
| 5,584,815 A | 12/1996 | Pawelka et al. |
| 5,602,171 A | 2/1997 | Tang et al. |
| 5,607,418 A | 3/1997 | Arzbaecher |
| 5,614,642 A | 3/1997 | Tang et al. |
| 5,616,123 A | 4/1997 | Cheikh et al. |
| 5,628,908 A | 5/1997 | Kamen et al. |
| 5,634,896 A | 6/1997 | Bryant et al. |
| 5,635,387 A | 6/1997 | Fei et al. |
| 5,637,095 A | 6/1997 | Nason et al. |
| 5,637,099 A | 6/1997 | Durdin et al. |
| 5,641,892 A | 6/1997 | Larkins et al. |
| 5,647,853 A | 7/1997 | Feldmann et al. |
| 5,647,854 A | 7/1997 | Olsen et al. |
| 5,655,897 A | 8/1997 | Neftel et al. |
| 5,656,032 A | 8/1997 | Kriesel et al. |
| 5,658,250 A | 8/1997 | Blomquist et al. |
| 5,658,252 A | 8/1997 | Johnson |
| 5,660,846 A | 8/1997 | Cheikh et al. |
| 5,665,065 A | 9/1997 | Colman et al. |
| 5,665,070 A | 9/1997 | McPhee |
| 5,669,877 A | 9/1997 | Blomquist |
| 5,672,167 A | 9/1997 | Athayde et al. |
| 5,693,018 A | 12/1997 | Kriesel et al. |
| 5,694,919 A | 12/1997 | Rubsamen et al. |
| 5,695,473 A | 12/1997 | Olsen |
| 5,700,244 A | 12/1997 | Kriesel |
| 5,700,904 A | 12/1997 | Baker et al. |
| 5,702,372 A | 12/1997 | Nelson |
| 5,707,361 A | 1/1998 | Slettenmark et al. |
| 5,713,865 A | 2/1998 | Manning et al. |
| 5,716,343 A | 2/1998 | Kriesel et al. |
| 5,718,568 A | 2/1998 | Neftel et al. |
| 5,722,397 A | 3/1998 | Eppstein |
| 5,722,956 A | 3/1998 | Sims et al. |
| 5,735,263 A | 4/1998 | Rubsamen et al. |
| 5,738,658 A | 4/1998 | Maus et al. |
| 5,741,125 A | 4/1998 | Neftel et al. |
| 5,749,835 A | 5/1998 | Glantz |
| 5,755,683 A | 5/1998 | Houle et al. |
| 5,764,159 A | 6/1998 | Neftel et al. |
| 5,772,409 A | 6/1998 | Johnson |
| 5,776,103 A | 7/1998 | Kriesel et al. |
| 5,777,060 A | 7/1998 | Van Antwerp |
| 5,782,798 A | 7/1998 | Rise |
| 5,785,681 A | 7/1998 | Indravudh |
| 5,785,688 A | 7/1998 | Joshi et al. |
| 5,788,671 A | 8/1998 | Johnson |
| 5,788,673 A | 8/1998 | Young et al. |
| 5,788,678 A | 8/1998 | Van Antwerp |
| 5,792,123 A | 8/1998 | Ensminger |
| 5,800,420 A | 9/1998 | Gross et al. |
| 5,800,421 A | 9/1998 | Lemelson |
| 5,807,315 A | 9/1998 | Van Antwerp et al. |
| 5,807,375 A | 9/1998 | Gross et al. |
| 5,810,015 A | 9/1998 | Flaherty |
| 5,810,771 A | 9/1998 | Blomquist |
| 5,820,622 A | 10/1998 | Gross et al. |
| 5,823,746 A | 10/1998 | Johnson |
| 5,827,262 A | 10/1998 | Neftel et al. |
| 5,837,234 A | 11/1998 | Gentile et al. |
| 5,837,276 A | 11/1998 | Cheikh et al. |
| 5,837,680 A | 11/1998 | Moses et al. |
| 5,843,023 A | 12/1998 | Cecchi |
| 5,848,990 A | 12/1998 | Cirelli et al. |
| 5,851,197 A | 12/1998 | Marano et al. |
| 5,858,001 A | 1/1999 | Tsals et al. |
| 5,858,969 A | 1/1999 | Marsh, Jr. et al. |
| 5,868,711 A | 2/1999 | Kramer et al. |
| 5,873,857 A | 2/1999 | Kriesel |
| 5,876,370 A | 3/1999 | Blomquist |
| 5,879,143 A | 3/1999 | Cote et al. |
| 5,882,494 A | 3/1999 | Van Antwerp |
| 5,891,086 A | 4/1999 | Weston |
| 5,906,592 A | 5/1999 | Kriesel et al. |
| 5,921,962 A | 7/1999 | Kriesel et al. |
| 5,928,196 A | 7/1999 | Johnson et al. |
| 5,935,099 A | 8/1999 | Peterson et al. |

(56) References Cited

U.S. PATENT DOCUMENTS

| | | | |
|---|---|---|---|
| 5,935,105 A | 8/1999 | Manning et al. | |
| 5,935,106 A | 8/1999 | Olsen | |
| 5,935,598 A | 8/1999 | Sage et al. | |
| 5,944,695 A | 8/1999 | Johnson et al. | |
| 5,951,521 A | 9/1999 | Mastrototaro et al. | |
| 5,952,347 A | 9/1999 | Arison et al. | |
| 5,954,485 A | 9/1999 | Johnson et al. | |
| 5,954,695 A | 9/1999 | Sims et al. | |
| 5,957,890 A | 9/1999 | Mann et al. | |
| 5,957,895 A | 9/1999 | Sage et al. | |
| 5,960,797 A | 10/1999 | Kramer et al. | |
| 5,961,499 A | 10/1999 | Bonutti et al. | |
| 5,968,014 A | 10/1999 | Neftel et al. | |
| 5,976,109 A | 11/1999 | Heruth | |
| 5,989,423 A | 11/1999 | Kamen et al. | |
| 5,995,860 A | 11/1999 | Sun et al. | |
| 6,002,954 A | 12/1999 | Van Antwerp et al. | |
| 6,006,753 A * | 12/1999 | Efendic | 128/898 |
| 6,007,555 A | 12/1999 | Devine | |
| 6,011,984 A | 1/2000 | Van Antwerp et al. | |
| 6,012,034 A | 1/2000 | Hamparian et al. | |
| 6,013,057 A | 1/2000 | Danby et al. | |
| 6,017,318 A | 1/2000 | Gauthier et al. | |
| 6,022,316 A | 2/2000 | Eppstein et al. | |
| 6,024,539 A | 2/2000 | Blomquist | |
| 6,025,331 A | 2/2000 | Moses et al. | |
| 6,030,399 A | 2/2000 | Ignotz et al. | |
| 6,040,194 A | 3/2000 | Chick et al. | |
| 6,041,801 A | 3/2000 | Gray et al. | |
| 6,043,273 A | 3/2000 | Duhaylongsod | |
| 6,045,734 A | 4/2000 | Luther et al. | |
| 6,048,328 A | 4/2000 | Haller et al. | |
| 6,049,727 A | 4/2000 | Crothall | |
| 6,051,557 A * | 4/2000 | Drucker | 514/12 |
| 6,053,893 A | 4/2000 | Bucher et al. | |
| 6,056,718 A | 5/2000 | Funderburk et al. | |
| 6,056,734 A | 5/2000 | Jacobsen et al. | |
| 6,057,131 A | 5/2000 | Marsh, Jr. et al. | |
| 6,059,753 A | 5/2000 | Faust et al. | |
| 6,065,941 A | 5/2000 | Gray et al. | |
| 6,068,613 A | 5/2000 | Kriesel et al. | |
| 6,070,761 A | 6/2000 | Bloom et al. | |
| 6,074,369 A | 6/2000 | Sage et al. | |
| 6,077,055 A | 6/2000 | Vilks | |
| 6,077,246 A | 6/2000 | Kullas et al. | |
| 6,077,248 A | 6/2000 | Zumschlinge et al. | |
| 6,077,259 A | 6/2000 | Caizza et al. | |
| 6,083,201 A | 7/2000 | Skinkle | |
| 6,085,574 A | 7/2000 | Neftel et al. | |
| 6,087,394 A | 7/2000 | Duhaylongsod | |
| 6,092,249 A | 7/2000 | Kamen et al. | |
| 6,093,167 A | 7/2000 | Houben et al. | |
| 6,093,172 A | 7/2000 | Funderburk et al. | |
| 6,110,152 A | 8/2000 | Kovelman | |
| 6,110,427 A | 8/2000 | Uffenheimer | |
| 6,110,721 A | 8/2000 | Gibbs et al. | |
| 6,112,111 A | 8/2000 | Glantz | |
| RE36,871 E | 9/2000 | Epstein et al. | |
| 6,120,460 A | 9/2000 | Abreu | |
| 6,122,536 A | 9/2000 | Sun et al. | |
| 6,123,668 A | 9/2000 | Abreu | |
| 6,123,685 A | 9/2000 | Reynolds | |
| 6,123,686 A | 9/2000 | Olsen et al. | |
| 6,126,642 A | 10/2000 | Kriesel et al. | |
| 6,127,410 A | 10/2000 | Duhaylongsod | |
| 6,135,978 A | 10/2000 | Houben et al. | |
| D434,142 S | 11/2000 | Cheney, II et al. | |
| 6,142,939 A | 11/2000 | Eppstein et al. | |
| 6,142,972 A | 11/2000 | Cheikh et al. | |
| 6,152,898 A | 11/2000 | Olsen | |
| 6,155,824 A | 12/2000 | Kamen et al. | |
| 6,165,154 A | 12/2000 | Gray et al. | |
| 6,168,609 B1 | 1/2001 | Kamen et al. | |
| 6,175,752 B1 | 1/2001 | Say et al. | |
| 6,183,434 B1 | 2/2001 | Eppstein | |
| 6,183,441 B1 | 2/2001 | Kriesel et al. | |
| 6,186,982 B1 | 2/2001 | Gross et al. | |
| 6,190,359 B1 | 2/2001 | Heruth | |
| 6,191,102 B1 * | 2/2001 | DiMarchi et al. | 514/2 |
| 6,193,704 B1 | 2/2001 | Winters | |
| 6,202,708 B1 | 3/2001 | Bynum | |
| 6,203,528 B1 | 3/2001 | Deckert et al. | |
| 6,206,850 B1 | 3/2001 | O'Neil et al. | |
| 6,207,856 B1 | 3/2001 | Veech | |
| 6,210,361 B1 | 4/2001 | Kamen et al. | |
| 6,213,943 B1 | 4/2001 | Abreu | |
| 6,214,617 B1 | 4/2001 | Herman | |
| 6,223,130 B1 | 4/2001 | Gray et al. | |
| 6,228,060 B1 | 5/2001 | Howell | |
| 6,231,320 B1 | 5/2001 | Lawless et al. | |
| 6,231,545 B1 | 5/2001 | Kriesel et al. | |
| 6,234,997 B1 | 5/2001 | Kamen et al. | |
| 6,241,704 B1 | 6/2001 | Peterson et al. | |
| 6,248,067 B1 | 6/2001 | Causey, III et al. | |
| 6,248,093 B1 | 6/2001 | Moberg | |
| 6,251,098 B1 | 6/2001 | Rake et al. | |
| 6,253,804 B1 | 7/2001 | Safabash | |
| 6,254,586 B1 | 7/2001 | Mann et al. | |
| 6,259,587 B1 | 7/2001 | Sheldon et al. | |
| 6,261,272 B1 | 7/2001 | Gross et al. | |
| 6,261,280 B1 | 7/2001 | Houben et al. | |
| 6,267,564 B1 | 7/2001 | Rapheal | |
| D446,854 S | 8/2001 | Cheney, II et al. | |
| 6,270,478 B1 | 8/2001 | Mernøe | |
| 6,280,416 B1 | 8/2001 | Van Antwerp et al. | |
| 6,283,943 B1 | 9/2001 | Dy et al. | |
| 6,283,944 B1 | 9/2001 | McMullen et al. | |
| 6,284,725 B1 | 9/2001 | Coolidge et al. | |
| 6,284,727 B1 * | 9/2001 | Kim et al. | 514/12 |
| 6,287,294 B1 | 9/2001 | Lemelson | |
| 6,287,521 B1 | 9/2001 | Quay et al. | |
| 6,293,925 B1 | 9/2001 | Safabash et al. | |
| 6,302,653 B1 | 10/2001 | Bryant et al. | |
| 6,302,990 B1 | 10/2001 | Nelson | |
| 6,306,420 B1 | 10/2001 | Cheikh et al. | |
| 6,312,393 B1 | 11/2001 | Abreu | |
| 6,315,769 B1 | 11/2001 | Peer et al. | |
| 6,316,038 B1 | 11/2001 | Veech | |
| 6,319,540 B1 | 11/2001 | Van Antwerp et al. | |
| 6,321,597 B1 | 11/2001 | Demers et al. | |
| 6,323,237 B1 | 11/2001 | Veech | |
| 6,329,336 B1 | 12/2001 | Bridon et al. | |
| 6,334,856 B1 | 1/2002 | Allen et al. | |
| 6,338,730 B1 | 1/2002 | Bonutti et al. | |
| D453,830 S | 2/2002 | McDowell et al. | |
| 6,343,614 B1 | 2/2002 | Gray et al. | |
| 6,346,095 B1 | 2/2002 | Gross et al. | |
| 6,348,043 B1 | 2/2002 | Hagen et al. | |
| 6,355,019 B1 | 3/2002 | Kriesel et al. | |
| 6,355,021 B1 | 3/2002 | Nielsen et al. | |
| 6,360,888 B1 | 3/2002 | McIvor et al. | |
| 6,362,591 B1 | 3/2002 | Moberg | |
| 6,364,279 B1 | 4/2002 | Neftel et al. | |
| 6,364,857 B1 | 4/2002 | Gray et al. | |
| 6,368,274 B1 | 4/2002 | Van Antwerp et al. | |
| 6,374,876 B2 | 4/2002 | Bynum | |
| 6,375,459 B1 | 4/2002 | Kamen et al. | |
| 6,375,638 B2 | 4/2002 | Nason et al. | |
| 6,379,345 B1 | 4/2002 | Constantz | |
| 6,382,923 B1 | 5/2002 | Gray | |
| 6,394,981 B2 | 5/2002 | Heruth | |
| 6,403,558 B1 | 6/2002 | Moses et al. | |
| 6,406,455 B1 | 6/2002 | Willis et al. | |
| 6,414,018 B1 | 7/2002 | Duhaylongsod | |
| 6,416,293 B1 | 7/2002 | Bouchard et al. | |
| 6,416,495 B1 | 7/2002 | Kriesel et al. | |
| 6,416,496 B1 | 7/2002 | Rogers et al. | |
| 6,422,057 B1 | 7/2002 | Anderson | |
| 6,423,001 B1 | 7/2002 | Abreu | |
| 6,423,035 B1 | 7/2002 | Das et al. | |
| 6,424,847 B1 | 7/2002 | Mastrototaro et al. | |
| 6,427,088 B1 | 7/2002 | Bowman, IV et al. | |
| D461,241 S | 8/2002 | Moberg et al. | |
| D461,891 S | 8/2002 | Moberg | |

(56) References Cited

U.S. PATENT DOCUMENTS

| | | | |
|---|---|---|---|
| 6,429,197 | B1 | 8/2002 | Coolidge et al. |
| 6,432,383 | B1 * | 8/2002 | Modi .............................. 424/43 |
| 6,436,072 | B1 | 8/2002 | Kullas et al. |
| 6,440,933 | B1 | 8/2002 | Bodor et al. |
| 6,443,942 | B2 | 9/2002 | Van Antwerp et al. |
| 6,453,956 | B2 | 9/2002 | Safabash |
| 6,458,102 | B1 | 10/2002 | Mann et al. |
| 6,458,355 | B1 | 10/2002 | Hsei et al. |
| 6,461,329 | B1 | 10/2002 | Van Antwerp et al. |
| 6,461,331 | B1 | 10/2002 | Van Antwerp |
| 6,464,667 | B1 | 10/2002 | Kamen et al. |
| 6,464,671 | B1 | 10/2002 | Elver et al. |
| 6,465,431 | B1 | 10/2002 | Thorn et al. |
| 6,468,532 | B1 | 10/2002 | Hsei et al. |
| 6,471,436 | B1 | 10/2002 | Gjata et al. |
| 6,471,674 | B1 | 10/2002 | Emig et al. |
| 6,475,180 | B2 | 11/2002 | Peterson et al. |
| 6,475,196 | B1 | 11/2002 | Vachon |
| 6,485,263 | B1 | 11/2002 | Bryant et al. |
| 6,485,461 | B1 | 11/2002 | Mason et al. |
| 6,485,465 | B2 | 11/2002 | Moberg et al. |
| 6,495,366 | B1 | 12/2002 | Briggs |
| 6,495,532 | B1 | 12/2002 | Bathurst et al. |
| 6,500,150 | B1 | 12/2002 | Gross et al. |
| 6,503,062 | B1 | 1/2003 | Gray et al. |
| 6,503,184 | B1 | 1/2003 | Ni et al. |
| 6,503,231 | B1 | 1/2003 | Prausnitz et al. |
| 6,505,059 | B1 | 1/2003 | Kollias et al. |
| 6,512,939 | B1 | 1/2003 | Colvin et al. |
| 6,514,500 | B1 | 2/2003 | Bridon et al. |
| 6,520,326 | B2 | 2/2003 | McIvor et al. |
| 6,520,747 | B2 | 2/2003 | Gray et al. |
| 6,520,936 | B1 | 2/2003 | Mann |
| 6,520,938 | B1 | 2/2003 | Funderburk et al. |
| D471,352 | S | 3/2003 | Shetler et al. |
| 6,527,716 | B1 | 3/2003 | Eppstein |
| 6,530,900 | B1 | 3/2003 | Daily et al. |
| 6,537,268 | B1 | 3/2003 | Gibson et al. |
| 6,544,193 | B2 | 4/2003 | Abreu |
| 6,544,229 | B1 | 4/2003 | Danby et al. |
| 6,551,276 | B1 | 4/2003 | Mann et al. |
| 6,554,798 | B1 | 4/2003 | Mann et al. |
| 6,554,800 | B1 | 4/2003 | Nezhadian et al. |
| 6,555,986 | B2 | 4/2003 | Moberg |
| 6,558,320 | B1 | 5/2003 | Causey, III et al. |
| 6,558,343 | B1 | 5/2003 | Neftel et al. |
| 6,558,345 | B1 | 5/2003 | Houben et al. |
| 6,558,351 | B1 | 5/2003 | Steil et al. |
| 6,560,471 | B1 | 5/2003 | Heller et al. |
| 6,562,001 | B2 | 5/2003 | Lebel et al. |
| 6,564,105 | B2 | 5/2003 | Starkweather et al. |
| 6,565,509 | B1 | 5/2003 | Say et al. |
| 6,565,531 | B1 | 5/2003 | Mori et al. |
| 6,565,534 | B1 | 5/2003 | Winters |
| 6,565,535 | B2 | 5/2003 | Zaias et al. |
| 6,565,885 | B1 | 5/2003 | Tarara et al. |
| 6,571,128 | B2 | 5/2003 | Lebel et al. |
| 6,572,586 | B1 | 6/2003 | Wojcik |
| 6,577,899 | B2 | 6/2003 | Lebel et al. |
| 6,579,690 | B1 | 6/2003 | Bonnecaze et al. |
| 6,585,644 | B2 | 7/2003 | Lebel et al. |
| 6,585,695 | B1 | 7/2003 | Adair et al. |
| 6,586,401 | B1 | 7/2003 | Thorn et al. |
| 6,589,229 | B1 * | 7/2003 | Connelly et al. ............ 604/890.1 |
| 6,589,936 | B1 | 7/2003 | Thorn et al. |
| 6,591,876 | B2 | 7/2003 | Safabash |
| 6,593,295 | B2 | 7/2003 | Bridon et al. |
| 6,595,202 | B2 | 7/2003 | Ganan-Calvo et al. |
| 6,595,756 | B2 | 7/2003 | Gray et al. |
| 6,595,956 | B1 | 7/2003 | Gross et al. |
| 6,604,908 | B1 | 8/2003 | Bryant et al. |
| 6,607,509 | B2 | 8/2003 | Bobroff et al. |
| 6,608,101 | B1 | 8/2003 | Ni et al. |
| 6,610,288 | B1 | 8/2003 | Edge et al. |
| 6,611,707 | B1 | 8/2003 | Prausnitz et al. |
| 6,613,026 | B1 | 9/2003 | Palasis et al. |
| 6,613,038 | B2 | 9/2003 | Bonutti et al. |
| 6,616,627 | B2 | 9/2003 | Willis et al. |
| 6,617,450 | B1 | 9/2003 | Stocker et al. |
| 6,622,732 | B2 | 9/2003 | Constantz |
| 6,629,954 | B1 | 10/2003 | Heruth |
| 6,632,215 | B1 | 10/2003 | Lemelson |
| 6,635,049 | B1 | 10/2003 | Robinson et al. |
| 6,635,743 | B1 | 10/2003 | Ebner et al. |
| 6,641,533 | B2 | 11/2003 | Causey, III et al. |
| 6,641,562 | B1 | 11/2003 | Peterson |
| 6,642,015 | B2 | 11/2003 | Vachon et al. |
| 6,645,175 | B2 | 11/2003 | Kriesel et al. |
| 6,648,821 | B2 | 11/2003 | Lebel et al. |
| 6,651,656 | B2 | 11/2003 | Demers et al. |
| 6,652,493 | B1 | 11/2003 | Das |
| 6,652,510 | B2 | 11/2003 | Lord et al. |
| 6,653,283 | B1 | 11/2003 | Moses et al. |
| 6,656,148 | B2 | 12/2003 | Das et al. |
| 6,656,158 | B2 | 12/2003 | Mahoney et al. |
| 6,656,159 | B2 | 12/2003 | Flaherty |
| 6,659,948 | B2 | 12/2003 | Lebel et al. |
| 6,659,982 | B2 | 12/2003 | Douglas et al. |
| 6,660,509 | B1 | 12/2003 | Herman et al. |
| 6,663,359 | B2 | 12/2003 | Gray |
| 6,665,909 | B2 | 12/2003 | Collins et al. |
| 6,666,845 | B2 | 12/2003 | Hooper et al. |
| 6,669,663 | B1 | 12/2003 | Thompson |
| 6,669,668 | B1 | 12/2003 | Kleeman et al. |
| 6,669,669 | B2 * | 12/2003 | Flaherty et al. ................ 604/132 |
| 6,671,554 | B2 | 12/2003 | Gibson et al. |
| 6,685,664 | B2 | 2/2004 | Levin et al. |
| 6,687,546 | B2 | 2/2004 | Lebel et al. |
| 6,689,073 | B2 | 2/2004 | Quay |
| 6,689,100 | B2 | 2/2004 | Connelly et al. |
| 6,689,108 | B2 | 2/2004 | Lavi et al. |
| 6,689,607 | B2 | 2/2004 | Ni et al. |
| 6,689,747 | B2 | 2/2004 | Filvaroff et al. |
| 6,692,456 | B1 | 2/2004 | Eppstein et al. |
| 6,692,457 | B2 | 2/2004 | Flaherty |
| 6,694,191 | B2 | 2/2004 | Starkweather et al. |
| 6,699,218 | B2 | 3/2004 | Flaherty et al. |
| 6,699,219 | B2 | 3/2004 | Emig et al. |
| 6,702,779 | B2 | 3/2004 | Connelly et al. |
| 6,703,217 | B2 | 3/2004 | Herman et al. |
| 6,709,417 | B1 | 3/2004 | Houle et al. |
| 6,711,436 | B1 | 3/2004 | Duhaylongsod |
| 6,716,190 | B1 | 4/2004 | Glines et al. |
| 6,716,193 | B1 | 4/2004 | Neftel |
| 6,721,582 | B2 | 4/2004 | Trepagnier et al. |
| 6,723,072 | B2 | 4/2004 | Flaherty et al. |
| 6,726,656 | B2 | 4/2004 | Kamen et al. |
| 6,728,560 | B2 | 4/2004 | Kollias et al. |
| 6,733,446 | B2 | 5/2004 | Lebel et al. |
| 6,734,162 | B2 | 5/2004 | Van Antwerp et al. |
| 6,734,186 | B1 | 5/2004 | Maw et al. |
| 6,736,795 | B2 | 5/2004 | Michel |
| 6,737,401 | B2 | 5/2004 | Kim et al. |
| 6,740,059 | B2 | 5/2004 | Flaherty |
| 6,740,072 | B2 | 5/2004 | Starkweather et al. |
| 6,740,075 | B2 | 5/2004 | Lebel et al. |
| 6,740,655 | B2 | 5/2004 | Magee et al. |
| 6,749,403 | B2 | 6/2004 | Bryant et al. |
| 6,749,587 | B2 | 6/2004 | Flaherty |
| 6,750,311 | B1 | 6/2004 | Van Antwerp et al. |
| 6,752,299 | B2 | 6/2004 | Shetler et al. |
| 6,752,785 | B2 | 6/2004 | Van Antwerp et al. |
| 6,752,787 | B1 | 6/2004 | Causey, III et al. |
| 6,753,177 | B1 | 6/2004 | Stocker et al. |
| 6,753,328 | B2 | 6/2004 | Wands et al. |
| 6,755,811 | B1 | 6/2004 | Constantz |
| 6,758,810 | B2 | 7/2004 | Lebel et al. |
| 6,766,183 | B2 | 7/2004 | Walsh et al. |
| 6,768,425 | B2 | 7/2004 | Flaherty et al. |
| 6,770,067 | B2 | 8/2004 | Lorenzen et al. |
| 6,770,729 | B2 | 8/2004 | Van Antwerp |
| 6,774,120 | B1 | 8/2004 | Ferber et al. |
| 6,784,274 | B2 | 8/2004 | Van Antwerp et al. |
| 6,792,982 | B2 | 9/2004 | Lincoln et al. |

(56) References Cited

U.S. PATENT DOCUMENTS

| | | |
|---|---|---|
| 6,796,956 B2 | 9/2004 | Hartlaub et al. |
| 6,796,957 B2 | 9/2004 | Carpenter et al. |
| 6,800,071 B1 | 10/2004 | McConnell et al. |
| 6,800,663 B2 | 10/2004 | Asgarzadeh et al. |
| 6,801,420 B2 | 10/2004 | Talbot et al. |
| 6,804,544 B2 | 10/2004 | Van Antwerp et al. |
| 6,805,687 B2 | 10/2004 | Dextradeur et al. |
| 6,805,693 B2 | 10/2004 | Gray et al. |
| 6,808,369 B2 | 10/2004 | Gray et al. |
| 6,808,506 B2 | 10/2004 | Lastovich et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,715 B2 | 11/2004 | Bonutti et al. |
| 6,817,990 B2 | 11/2004 | Yap et al. |
| 6,821,949 B2 | 11/2004 | Bridon et al. |
| 6,824,529 B2 | 11/2004 | Gross et al. |
| 6,827,702 B2 | 12/2004 | Lebel et al. |
| 6,830,558 B2 | 12/2004 | Flaherty et al. |
| 6,830,564 B2 | 12/2004 | Gray |
| 6,840,922 B2 | 1/2005 | Nielsen et al. |
| 6,843,782 B2 | 1/2005 | Gross et al. |
| 6,849,718 B2 | 2/2005 | Kaelin, Jr. et al. |
| 6,849,719 B2 | 2/2005 | Shi et al. |
| 6,902,544 B2 | 6/2005 | Ludin et al. |
| 6,936,029 B2 | 8/2005 | Mann et al. |
| 6,939,324 B2 | 9/2005 | Gonnelli et al. |
| 6,960,184 B2 | 11/2005 | Willis et al. |
| 6,979,316 B1 | 12/2005 | Rubin et al. |
| 7,011,234 B2 | 3/2006 | Stradella |
| 7,014,625 B2 | 3/2006 | Bengtsson |
| 7,022,107 B1 | 4/2006 | Christensen et al. |
| 7,108,686 B2 | 9/2006 | Burke et al. |
| 7,150,409 B2 | 12/2006 | Gonnelli et al. |
| 7,204,823 B2 | 4/2007 | Estes et al. |
| 7,250,037 B2 | 7/2007 | Shermer et al. |
| 7,337,922 B2 | 3/2008 | Rake et al. |
| 7,367,968 B2 | 5/2008 | Rosenberg et al. |
| 7,481,792 B2 | 1/2009 | Gonnelli et al. |
| 7,530,968 B2 | 5/2009 | Gonnelli |
| 7,534,226 B2 | 5/2009 | Mernoe et al. |
| 7,678,079 B2 | 3/2010 | Shermer et al. |
| 2001/0005781 A1 | 6/2001 | Bergens et al. |
| 2001/0010238 A1 | 8/2001 | Bynum |
| 2001/0016710 A1 | 8/2001 | Nason et al. |
| 2001/0027287 A1 | 10/2001 | Shmulewitz et al. |
| 2001/0031944 A1 | 10/2001 | Peterson et al. |
| 2001/0037083 A1 | 11/2001 | Hartlaub et al. |
| 2001/0053891 A1 | 12/2001 | Ackley |
| 2001/0056259 A1 | 12/2001 | Skinkle et al. |
| 2002/0004015 A1 | 1/2002 | Carlisle et al. |
| 2002/0019612 A1 | 2/2002 | Watanabe et al. |
| 2002/0040208 A1 | 4/2002 | Flaherty et al. |
| 2002/0045867 A1 | 4/2002 | Nielsen et al. |
| 2002/0055460 A1 | 5/2002 | Coolidge et al. |
| 2002/0061838 A1 | 5/2002 | Holmquist et al. |
| 2002/0072733 A1* | 6/2002 | Flaherty ............... 604/890.1 |
| 2002/0077599 A1 | 6/2002 | Wojcik |
| 2002/0091358 A1 | 7/2002 | Klitmose |
| 2002/0095124 A1 | 7/2002 | Palasis et al. |
| 2002/0123716 A1 | 9/2002 | VanDiver et al. |
| 2002/0123740 A1* | 9/2002 | Flaherty et al. ....... 604/890.1 |
| 2002/0128594 A1 | 9/2002 | Das et al. |
| 2002/0138049 A1 | 9/2002 | Allen et al. |
| 2002/0147131 A1 | 10/2002 | Coolidge et al. |
| 2002/0151842 A1 | 10/2002 | Gonnelli et al. |
| 2002/0151846 A1 | 10/2002 | Christenson et al. |
| 2002/0156418 A1 | 10/2002 | Gonnelli et al. |
| 2002/0156464 A1 | 10/2002 | Blischak et al. |
| 2002/0177809 A1 | 11/2002 | Kriesel et al. |
| 2002/0183693 A1 | 12/2002 | Peterson et al. |
| 2002/0188259 A1 | 12/2002 | Hickle et al. |
| 2002/0198493 A1 | 12/2002 | Diaz et al. |
| 2002/0198494 A1 | 12/2002 | Diaz et al. |
| 2003/0009133 A1 | 1/2003 | Ramey |
| 2003/0022823 A1* | 1/2003 | Efendic .................... 514/12 |
| 2003/0024508 A1 | 2/2003 | Heller et al. |
| 2003/0050237 A1* | 3/2003 | Kim et al. ................ 514/12 |
| 2003/0050623 A1 | 3/2003 | Lord et al. |
| 2003/0073626 A1 | 4/2003 | Hathaway et al. |
| 2003/0100888 A1 | 5/2003 | Spinello |
| 2003/0125669 A1 | 7/2003 | Safabash et al. |
| 2003/0130619 A1 | 7/2003 | Safabash et al. |
| 2003/0130647 A1 | 7/2003 | Gray et al. |
| 2003/0135158 A1 | 7/2003 | Gonnelli |
| 2003/0135160 A1 | 7/2003 | Gray et al. |
| 2003/0158520 A1 | 8/2003 | Safabash et al. |
| 2003/0163223 A1* | 8/2003 | Blomquist ............... 700/282 |
| 2003/0167039 A1 | 9/2003 | Moberg |
| 2003/0195157 A1* | 10/2003 | Natarajan et al. ........... 514/16 |
| 2003/0199445 A1* | 10/2003 | Knudsen et al. ........... 514/12 |
| 2003/0199823 A1 | 10/2003 | Bobroff et al. |
| 2003/0212000 A1 | 11/2003 | Van Antwerp |
| 2003/0216714 A1* | 11/2003 | Gill .......................... 604/890.1 |
| 2003/0220610 A1 | 11/2003 | Lastovich et al. |
| 2003/0225373 A1 | 12/2003 | Bobroff et al. |
| 2003/0229309 A1 | 12/2003 | Babkes et al. |
| 2003/0233069 A1 | 12/2003 | Gillespie et al. |
| 2004/0002682 A1 | 1/2004 | Kovelman et al. |
| 2004/0029784 A1 | 2/2004 | Hathaway |
| 2004/0064086 A1 | 4/2004 | Gottlieb et al. |
| 2004/0064096 A1 | 4/2004 | Flaherty et al. |
| 2004/0064097 A1 | 4/2004 | Peterson |
| 2004/0073161 A1 | 4/2004 | Tachibana |
| 2004/0077000 A1 | 4/2004 | Stocker et al. |
| 2004/0085215 A1 | 5/2004 | Moberg et al. |
| 2004/0091374 A1 | 5/2004 | Gray |
| 2004/0092873 A1 | 5/2004 | Moberg |
| 2004/0092893 A1 | 5/2004 | Haider et al. |
| 2004/0094823 A1 | 5/2004 | Matsuno |
| 2004/0115067 A1 | 6/2004 | Rush et al. |
| 2004/0116905 A1 | 6/2004 | Pedersen et al. |
| 2004/0126372 A1 | 7/2004 | Banerjee et al. |
| 2004/0126373 A1 | 7/2004 | Banerjee et al. |
| 2004/0133163 A1 | 7/2004 | Schiffmann |
| 2004/0143216 A1 | 7/2004 | Douglas et al. |
| 2004/0143217 A1 | 7/2004 | Michel |
| 2004/0143218 A1 | 7/2004 | Das |
| 2004/0153032 A1 | 8/2004 | Garribotto et al. |
| 2004/0155079 A1 | 8/2004 | Shetler et al. |
| 2004/0167464 A1 | 8/2004 | Ireland et al. |
| 2004/0167470 A1 | 8/2004 | Emig et al. |
| 2004/0176725 A1 | 9/2004 | Stutz et al. |
| 2004/0209801 A1 | 10/2004 | Brand et al. |
| 2004/0220456 A1 | 11/2004 | Eppstein |
| 2004/0220525 A1 | 11/2004 | Willis et al. |
| 2004/0225281 A1 | 11/2004 | Lorenzen et al. |
| 2004/0247445 A1 | 12/2004 | Nelson et al. |
| 2004/0249363 A1 | 12/2004 | Burke et al. |
| 2004/0250382 A1 | 12/2004 | Collins et al. |
| 2004/0254525 A1 | 12/2004 | Uber et al. |
| 2004/0260234 A1 | 12/2004 | Srinivasan et al. |
| 2004/0266678 A1 | 12/2004 | Beeley et al. |
| 2004/0267201 A1 | 12/2004 | Agerup |
| 2005/0008661 A1 | 1/2005 | Fereira et al. |
| 2005/0024175 A1 | 2/2005 | Gray et al. |
| 2005/0033232 A1 | 2/2005 | Kriesel |
| 2005/0054988 A1 | 3/2005 | Rosenberg et al. |
| 2005/0065472 A1 | 3/2005 | Cindrich et al. |
| 2005/0070875 A1 | 3/2005 | Kulessa |
| 2005/0112188 A1 | 5/2005 | Eliaz et al. |
| 2005/0119618 A1 | 6/2005 | Gonnelli |
| 2005/0137530 A1 | 6/2005 | Campbell et al. |
| 2005/0137578 A1 | 6/2005 | Heruth et al. |
| 2005/0171477 A1 | 8/2005 | Rubin et al. |
| 2005/0171512 A1 | 8/2005 | Flaherty |
| 2005/0177109 A1 | 8/2005 | Azzolini |
| 2005/0215850 A1 | 9/2005 | Klein et al. |
| 2005/0234428 A1 | 10/2005 | Spohn et al. |
| 2005/0245904 A1 | 11/2005 | Estes et al. |
| 2005/0273083 A1 | 12/2005 | Lebel et al. |

(56) References Cited

U.S. PATENT DOCUMENTS

| | | |
|---|---|---|
| 2005/0277912 A1 | 12/2005 | John |
| 2005/0278073 A1 | 12/2005 | Roth |
| 2006/0030838 A1 | 2/2006 | Gonnelli |
| 2006/0069382 A1 | 3/2006 | Pederson |
| 2006/0079862 A1 | 4/2006 | Genosar |
| 2006/0100578 A1 | 5/2006 | Lieberman |
| 2006/0122628 A1 | 6/2006 | Solar et al. |
| 2006/0150747 A1 | 7/2006 | Mallet |
| 2006/0184119 A1 | 8/2006 | Remde et al. |
| 2006/0184154 A1 | 8/2006 | Moberg et al. |
| 2006/0189939 A1 | 8/2006 | Gonnelli et al. |
| 2006/0200112 A1 | 9/2006 | Paul |
| 2006/0264831 A1 | 11/2006 | Skwarek et al. |
| 2006/0264835 A1 | 11/2006 | Nielsen et al. |
| 2007/0016170 A1 | 1/2007 | Kovelman |
| 2007/0060894 A1 | 3/2007 | Dai et al. |
| 2007/0073236 A1 | 3/2007 | Mernoe et al. |
| 2007/0088268 A1 | 4/2007 | Edwards |
| 2007/0100283 A1 | 5/2007 | Causey, III et al. |
| 2007/0149925 A1 | 6/2007 | Edwards et al. |
| 2007/0167912 A1 | 7/2007 | Causey et al. |
| 2007/0173761 A1 | 7/2007 | Kanderian, Jr. et al. |
| 2007/0179444 A1 | 8/2007 | Causey et al. |
| 2007/0239114 A1 | 10/2007 | Edwards et al. |
| 2007/0287958 A1 | 12/2007 | McKenzie et al. |
| 2007/0287985 A1 | 12/2007 | Estes et al. |
| 2008/0058719 A1 | 3/2008 | Edwards et al. |
| 2008/0091176 A1 | 4/2008 | Alessi et al. |
| 2008/0106431 A1 | 5/2008 | Blomquist |
| 2008/0125701 A1 | 5/2008 | Moberg et al. |
| 2008/0139910 A1 | 6/2008 | Mastrototaro et al. |
| 2008/0183060 A1 | 7/2008 | Steil et al. |
| 2008/0215006 A1 | 9/2008 | Thorkild |
| 2008/0249468 A1 | 10/2008 | Edwards et al. |
| 2008/0306436 A1 | 12/2008 | Edwards et al. |
| 2008/0312512 A1 | 12/2008 | Brukalo et al. |
| 2008/0319383 A1 | 12/2008 | Byland et al. |
| 2009/0054867 A1 | 2/2009 | Gravesen et al. |
| 2009/0062747 A1 | 3/2009 | Saul |
| 2009/0088689 A1 | 4/2009 | Carter |
| 2009/0088692 A1 | 4/2009 | Adams et al. |
| 2009/0093772 A1 | 4/2009 | Genosar et al. |
| 2009/0182277 A1 | 7/2009 | Carter |
| 2009/0202608 A1 | 8/2009 | Allessi et al. |
| 2009/0220358 A1 | 9/2009 | Krivsky et al. |
| 2009/0240232 A1 | 9/2009 | Gonnelli et al. |
| 2009/0247982 A1 | 10/2009 | Krulevitch et al. |
| 2009/0281528 A1 | 11/2009 | Grovender et al. |

FOREIGN PATENT DOCUMENTS

| | | |
|---|---|---|
| EP | 0209677 A1 | 1/1987 |
| EP | 0401179 A1 | 12/1990 |
| EP | 0513879 A2 | 11/1992 |
| EP | 0098592 A2 | 1/1994 |
| EP | 0638324 A1 | 2/1995 |
| EP | 0937475 A2 | 8/1999 |
| EP | 0902696 B1 | 3/2002 |
| EP | 1173197 B1 | 12/2004 |
| EP | 1512410 A1 | 3/2005 |
| EP | 1210136 B1 | 1/2006 |
| GB | 2 054 381 | 2/1981 |
| JP | 62270167 | 11/1987 |
| NL | 7310455 A | 2/1974 |
| RU | 2248223 C2 | 3/2005 |
| WO | WO-97/28835 | 8/1997 |
| WO | 8503232 A1 | 1/1998 |
| WO | WO 98/08871 A1 | 3/1998 |
| WO | 9810129 A1 | 12/1998 |
| WO | 9948546 A | 9/1999 |
| WO | WO 99/47161 A1 | 9/1999 |
| WO | WO 00/66138 A2 | 11/2000 |
| WO | WO 00/66142 A2 | 11/2000 |
| WO | WO 01/00223 A2 | 1/2001 |
| WO | WO 01/87322 A2 | 11/2001 |
| WO | WO 02/085406 A1 | 10/2002 |
| WO | WO 03/008023 A1 | 1/2003 |
| WO | 2003050846 A3 | 6/2003 |
| WO | WO 03/061362 A2 | 7/2003 |
| WO | WO 03/080160 A1 | 10/2003 |
| WO | WO 2004/037195 A2 | 5/2004 |
| WO | WO 2004/089335 A2 | 10/2004 |
| WO | 2004/094823 A2 | 11/2004 |
| WO | WO 2004094823 A2 * | 11/2004 |
| WO | WO 2005/046716 A1 | 5/2005 |
| WO | WO 2005/048952 A2 | 6/2005 |
| WO | WO 2005/060986 A1 | 7/2005 |
| WO | 2007051139 A2 | 5/2007 |
| WO | 2007129317 A1 | 11/2007 |
| WO | 2008036509 A3 | 3/2008 |
| WO | 2008139458 A3 | 11/2008 |
| WO | 2009013735 A1 | 1/2009 |
| WO | 2009016637 A1 | 2/2009 |
| WO | 2009081403 A2 | 7/2009 |
| WO | 2009125398 A2 | 10/2009 |

OTHER PUBLICATIONS

Capaldi, Treatments and devices for future diabetes management. Nurs Times. 101(18): 30-2, 2005.
Choi et al., Control of blood glucose by novel GLP-1 delivery using biodegradable triblock copolymer of PLGA-PEG-PLGA in type 2 diabetic rats. Pharm Res. 21(5): 827-31, 2004.
Donahey et al., Intraventricular GLP-1 reduces short- but not long-term food intake or body weight in lean and obese rats. Brain Res. 779(1-2): 75-83, 1998.
Drucker, Development of glucagon-like peptide-1-based pharmaceuticals as therapeutic agents for the treatment of diabetes. Curr Pharm Des. 7(14): 1399-412, 2001.
Gappa et al., The effect of zinc-crystallized glucagon-like peptide-1 on insulin secretion of macroencapsulated pancreatic islets. Tissue Eng. 7(1): 35-44, 2001.
Haak, New developments in the treatment of type 1 diabetes mellitus. Exp Clin Endocrinol Diabetes. 107 Suppl 3: S108-13, 1999.
Holst et al., On the treatment of diabetes mellitus with glucagon-like peptide-1. Ann NY Acad Sci. 865: 336-43, 1998.
Hui et al., The short half-life of glucagon-like peptide-1 in plasma does not reflect its long-lasting beneficial effects. Eur J Endocrinol. 146(6): 863-9, 2002.
Joseph et al., Oral delivery of glucagon-like peptide-1 in a modified polymer preparation normalizes basal glycaemia in diabetic db/db mice. Diabetologia. 43(10): 1319-28, 2000.
Toft-Nielsen et al., Continuous subcutaneous infusion of glucagon-like peptide 1 lowers plasma glucose and reduces appetite in type 2 diabetic patients. Diabetes Care. 22(7): 1137-43, 1999.
Wang et al., Glucagon-like peptide-1 can reverse the age-related decline in glucose tolerance in rats. J Clin Invest. 99(12): 2883-9, 1997.
Gonnelli, Robert R. Barnett International Needle-Free Injection Systems presentation materials, Mar. 25, 2004, BioValve Technologies, Inc. (10 pages).
Singapore Written Opinion from Singapore Pat. App. No. 2008070302-5 dated Jan. 6, 2010.
International Search Report for PCT/US2007/65363 dated Sep. 18, 2008.
Office Action for U.S. Appl. No. 12/295,173 dated Jan. 26, 2010.
USPTO Non-Final Rejection mailed Jun. 10, 2010 in connection with U.S. Appl. No. 12/295,173.
Office Action for U.S. Appl. No. 12/336,395 dated Sep. 21, 2011.
International Search Report and Written Opinion mailed Dec. 10, 2010 in connection with International Application No. PCT/US10/52352.
English Translation of First Office Action issued in connection with Chinese Application No. 200780020245.9.
First EPO Examination Report issued in connection with European Application No. 01988242.2.
Final Office Action dated Sep. 12, 2014 for U.S. Appl. No. 12/762,307.

* cited by examiner

METHODS AND DEVICES FOR DELIVERING GLP-1 AND USES THEREOF

REFERENCE TO RELATED APPLICATION

This application claims the benefit of the filing date of U.S. Provisional Application 60/585,330, filed on Jul. 2, 2004, the entire content of which is incorporated herein by reference.

BACKGROUND OF THE INVENTION

Glucagon-like peptide-1 (GLP-1) is a relatively recently discovered gastrointestinal hormone (Holst, Gastroenterology 107: 1848-1855, 1994) that has attracted considerable interest because of its potent actions on carbohydrate metabolism and its potential use as a therapeutic agent in the treatment of type-2 diabetes (Gutniak et al., N. Engl. J. Med. 326: 1316-1322, 1992; Nathan et al., Diabetes Care 15: 270-276, 1992). It arises from tissue-specific processing of the glucagon precursor, proglucagon, within the L-cell of the distal intestinal mucosa (Bell et al., Nature (London) 304: 368-371, 1983; Mojsov et al., J. Biol. Chem. 261: 11800-11889, 1986; Orskov et al., Endocrinology 119: 1467-1475, 1986), from which it is secreted in response to meal ingestion (Elliott et al., J. Endocrinol. 38: 159-166, 1993; Herrmann et al., Digestion 56: 117-126, 1995; Orskov et al., Scand. J. Gastroenterol. 31: 665-670, 1996).

The processing pattern of proglucagon leading to the formation of GLP-1 is known in detail (Bell, supra; Mojsov, supra; Ørskov et al., Endocrinology 119: 1467-1475, 1986; Ørskov et al., Diabetes. 43: 535-539, 1994; Ørskov et al., Diabetologia. 30: 874-881, 1987). Initial studies of GLP-1 biological activity in the mid 1980s utilized the full length N-terminal extended forms of GLP-1 (1-37 and 1-36amide). These larger GLP-1 molecules were generally devoid of biological activity. In 1987, 3 independent research groups demonstrated that removal of the first 6 amino acids resulted in a shorter version of the GLP-1 molecule with substantially enhanced biological activity. The majority of circulating biologically active GLP-1 is found in the GLP-1(7-36)amide form), with lesser amounts of the bioactive GLP-1(7-37) form also detectable. See Orskov et al. (Diabetes 43(4): 535-9, 1994) for the human data. Both peptides appear equipotent in all biological paradigms studied to date. GLP-1 is secreted from gut endocrine cells in response to nutrient ingestion and plays multiple roles in metabolic homeostasis following nutrient absorption.

Furthermore, the two naturally occurring truncated peptides, GLP-1(7-37)OH and GLP-1(7-36)$NH_2$, are rapidly cleared in vivo and have extremely short in vivo half-lives. In several studies (Deacon et al., J. Clin. Endocrinol. Metab. 80: 952-957, 1995; Deacon et al., Diabetes. 44: 1126-1131, 1995; Mentlein et al., Eur. J. Biochem. 214: 829-835, 1993), it was found that GLP-1, in addition to its renal and hepatic elimination (Deacon et al., Am. J. Physiol. Endocrinol. Metab. 34: E458-E464, 1996), is degraded in plasma by the enzyme dipeptidyl peptidase IV (DPP-IV). The enzyme removes a dipeptide from the N terminus of GLP-1 (Deacon, supra; Mentlein, supra), producing the truncated fragment GLP-1 (9-36)amide. This cleavage of GLP-1 seems to be relevant for its actions on the endocrine pancreas. Thus, in a recent study of the interaction of GLP-1 (9-36) amide with the cloned GLP-1 receptor, GLP-1 (9-36) amide antagonized the action of GLP-17-36 amide (Knudsen and Pridal, Eur. J. Pharmacol. 318: 429-435, 1996). In another study, after showing previously that GLP-1 strongly inhibited cephalic-induced antral motility in pigs, Wettergren et al. (Peptides 19(5): 877-882, 1998) reported that an intact N terminus is essential for the gastrointestinal actions of GLP-1, and that its primary metabolite, GLP-1 (9-36)amide, may even act as an endogenous antagonist.

Further, GLP-1 compound formulations currently in development cannot be given orally and like insulin, must be injected. Thus, despite the clear medical advantages associated with therapy involving GLP-1, the short half-life which results in a drug that must be injected one or more times a day has impeded commercial development efforts. Generally, moving patients to an injectable therapy is quite difficult. For example, many diabetics are unwilling to undertake any type of intensive injection therapy due to the discomfort associated with the many injections required to maintain adequate glucose control. Furthermore, diabetics on insulin are generally required to monitor their blood glucose, which involves additional needle sticks. This type of therapy can be both psychologically and physically painful. This is especially true when patients have been treated solely with oral medications throughout the progression of the disease.

Therefore, there is a need in the art for more effective ways to deliver GLP-1 to patients in need thereof, preferably through less-invasive delivery means, so as to overcome or at least reduce several problems associated with GLP-1 therapy, such as the potentially inhibitory function of the natural metabolites of GLP-1, and the painful and invasive delivery means.

BRIEF DESCRIPTION OF THE DRAWINGS

The present disclosure may be better understood and its numerous features and advantages made apparent to those skilled in the art by referencing the accompanying drawings.

The use of the same reference symbols in different drawings indicates similar or identical items.

SUMMARY OF THE INVENTION

Figure 1:
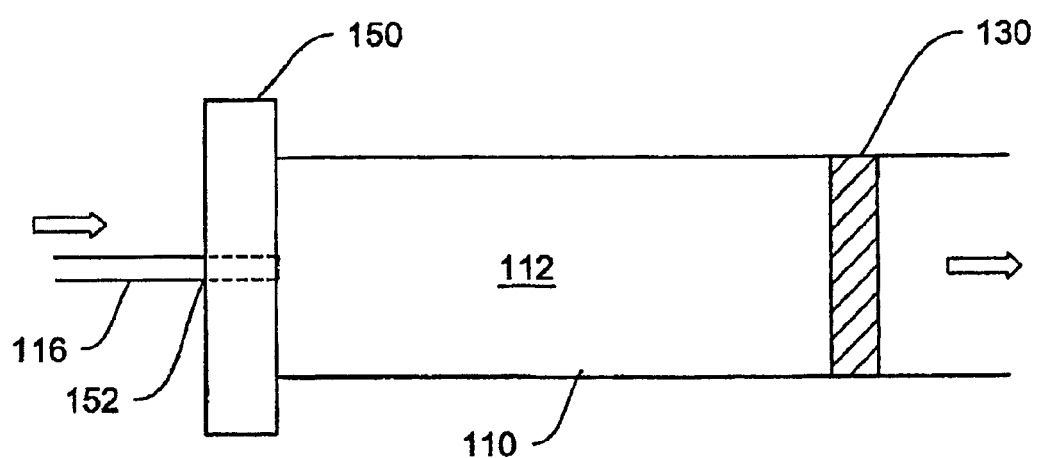
FIG. 1 is a high-level functional schematic drawing of a hydraulic pump system, according to one embodiment of the invention.

Disclosed herein are systems, methods, apparatus, and reagents for delivering GLP-1 and its analogs or derivative compounds to a human or non-human mammalian patient using a pump, partly to overcome the difficulty of treating such patients with GLP-1 associated with the short half-life of GLP-1, especially the short half-life of GLP-1 in vivo.

The subject drug delivery systems (comprising a drug/device combination) provide a means to deliver GLP-1 compounds at various dosage schemes, quantity, and speed, preferably over a sustained period of time, so as to ensure the most effective amount of GLP-1 compounds in vivo to achieve optimum efficacy.

Thus one aspect of the invention provides a system for delivering an effective amount of a GLP-1 compound to a patient in need of GLP-1 receptor stimulation, the system comprising:

(1) a pump-driven fluid delivery device; (2) a liquid form of said GLP-1 compound stored in said pump-driven fluid delivery device.

In one embodiment, the pump-driven fluid delivery device comprises: (1) a pump chamber, and a fluid storage chamber having an orifice and being functionally connected to said pump chamber by a moveable barrier; (2) a hydraulic fluid reservoir for storing a high viscosity fluid, said reservoir being connected to said pump chamber via a restrictor capable of controlling the rate of flow of the high viscosity fluid, and, (3) an actuator functionally connected to said hydraulic fluid reservoir to cause said hydraulic fluid to flow into said pump chamber through said restrictor, thereby expanding the volume of said pump chamber, displacing said moveable barrier and causing a quantity of said liquid component stored in said fluid storage chamber to be delivered at a sustained rate.

In other embodiments, other pump devices, such as those described herein, with their various embodiments, can also be used to in the subject drug-device combination to deliver GLP-1 compounds.

Another aspect of the invention provides a method of stimulating a GLP-1 receptor in a subject in need of such stimulation, said method comprising the step of administering to a patient an effective amount of a GLP-1 compound using a pump-driven fluid delivery device with a liquid form of said GLP-1 compound stored therein.

In one embodiment, the GLP-1 compound is GLP-1.

In one embodiment, the GLP-1 compound is a GLP-1 analog with substantially the same or better potency than that of GLP-1.

In one embodiment, the GLP-1 compound is a derivative of GLP-1 or GLP-1 analog, with substantially the same or better potency than that of GLP-1.

In one embodiment, the GLP-1 compound is delivered continuously.

In one embodiment, the rate of delivery is equivalent to about 0.25 to 6 pmol/kg body weight/min., preferably from about 0.5 to about 1.2 pmol/kg/min., or from about 0.6 to about 2.4 pmol/kg/min. of GLP-1.

In one embodiment, the GLP-1 compound is delivered intermitantly.

In one embodiment, the rate of delivery, as averaged over the entire delivery period, is equivalent to about 0.25 to 6 pmol/kg body weight/min., preferably from about 0.5 to about 1.2 pmol/kg/min., or from about 0.6 to about 2.4 pmol/kg/min. of GLP-1.

In one embodiment, the entire delivery period for said GLP-1 compound is about 6 hrs, about 12 hrs, about 1 day, about 3 days, about 5 days, about 2 weeks, about 1 month, about 3 months, about 6 months, about 1 year or more.

It is contemplated that each embodiment can be combined with other embodiments whenever appropriate.

DETAILED DESCRIPTION OF THE INVENTION

Various systems, devices and methods are provided for more effective administration of GLP-1 to a patient in need thereof, which allow administration of GLP-1 therapeutics in continuous, or otherwise predetermined pattern, so as to achieve the maximum effect of stimulating insulin production by pancreatic beta cells without using toxic or near toxic levels of GLP-1. In particular, drug-device combinations (systems) are provided herein which enable more effective, less invasive administration of GLP-1.

For example, traditional bolus injection of GLP-1 may account for the high in vivo degredation rate of GLP-1, and requires administering a higher-than-necessary bolus dose of GLP-1 into the patient's system. This dose is limited by the maximal tolerable amount of GLP-1 in the patient's system. From there, the effective level of GLP-1 decreases in vivo, and may quickly drop below the effective range of GLP-1 concentration. This problem may be worse where the maximum tolerable dose may still fall below the most effective concentration of GLP-1. In that case, as soon as the GLP-1 therapeutic is administered, it starts to drift further away from the most effective range in vivo. Thus ideally, the concentration of GLP-1 should be kept near the maximal tolerable dose as long as possible/necessary.

The methods of the invention can be used to deliver GLP-1 at a continuous fashion, over a relatively long period of time.

In one embodiment, the patient has a condition characterized by abnormal carbohydrate metabolism, such as diabetes, especially type II diabetes.

In another embodiment, the patient has a condition characterized by excessive gastropancreatic secretion and gastric motility.

Transportation of molecules through the microneedles can be controlled or monitored using, for example, various combinations of valves, pumps, sensors, actuators, and microprocessors. These components can be produced using standard manufacturing or microfabrication techniques. Actuators that may be useful with the microneedle devices disclosed herein include micropumps, microvalves, and positioners. In a preferred embodiment, a microprocessor is programmed to control a pump or valve, thereby controlling the rate of delivery.

Hydraulic Pump for Long-Duration Sustained-Release of GLP-1

U.S. Ser. No. 60/465,070 (filed on Apr. 23, 2003, titled "HYDRAULICALLY ACTUATED PUMP FOR LONG DURATION MEDICAMENT ADMINISTRATION") and U.S. Ser. No. 10/831,354 (filed on Apr. 23, 2004, titled "HYDRAULICALLY ACTUATED PUMP FOR LONG DURATION MEDICAMENT ADMINISTRATION") describe a hydraulic actuated pump for long-duration sustained release of therapeutic agents (such as GLP-1) to a patient (the entire contents incorporated herein by reference). The hydraulic device is suitable for delivering a sustained flow of liquid, especially in small amounts and over a long period of time. Partly due to the hydraulic pressure system, the operation of the device is relatively insensitive to environmental changes, such as ambient temperature, altitude, or external pressure.

The hydraulic pump-driven drug delivery system provides pump devices for delivering a medicament, e.g., GLP-1 and analogs thereof to a patient, typically through the skin. To this end, the system includes an actuator that operates on a reservoir of viscous fluid. The actuator causes the viscous fluid to apply pressure to medicament to the medicament being delivered. The viscous fluid is controlled by a restrictor that, in one practice, controls the rate of flow of the fluid so that an uneven application of pressure to the reservoir is mediated, and a controlled rate of fluid movement is achieved. This controlled rate of fluid movement is employed to cause a medicament to be delivered at a selected rate.

In one embodiment the systems and methods described herein include a hydraulic pump system that may include a chamber (the "pump chamber") that can be filled with high viscosity fluid, which, when forced by pressure, enters the pump chamber through a restrictor, for example an opening/aperture, which is dimensionally adapted to control the rate of fluid flow therethrough. In one embodiment, the aperture is about the size of a 1-100 µm diameter circle (but not necessarily circular in shape). However, those of skill in the art will understand that any suitable restrictor may be employed, and that the size and the shape of the restrictor can vary to achieve the desired flow rate of the fluid being mediated under the expected conditions, including temperature and ambient pressure.

The increase in volume of the working fluid inside the pump chamber triggers the movement of a barrier mechanism, which can be coupled to other devices, such as a second, fluid storage chamber.

One advantage of the instant hydraulic pump system resides with the restrictor through which the high viscosity working fluid flows. For example, when the restrictor is an aperture, when subjected to varying pressure, the working fluid enters the chamber through the aperture at a slow, yet relatively constant rate, thus mostly eliminating the potentially large variations in the force generating the pressure, while ensuring a substantially less variable expansion in volume of the working fluid in the chamber. This in turn leads to a relatively smooth and constant movement of the coupled barrier mechanism.

An additional advantage of the hydraulic pump system is that its relatively low requirement for a constant pressure source, or its high ability to tolerate relatively large variations in force generated by the pressure source. This is especially useful in manufacturing simple and inexpensive devices, such as single-use, disposable devices for medical use.

Partly because of the over-pressure employed in the hydraulic pump system, a further advantage is that the hydraulic pump is relatively insensitive to environmental changes, such as ambient temperature, altitude, or external pressure.

One illustrative embodiment of the hydraulic fluid system described herein is shown in the high-level functional drawing of FIG. 1. The pump chamber 110 may be shaped like, but is not limited to, a cylinder. The hatched lines represent a moveable barrier 130, which may (but need not to) be at the distal end of aperture 152. Hydraulic fluid 112 enters aperture 152 on pump chamber wall 150 into pump chamber 110, optionally via a connective passage 116.

The hydraulic pump system can be employed in a fluid delivery system that can be manufactured inexpensively, and could take advantage of the slow, yet relatively constant delivery rate associated with the hydraulic pump system. Partly due to the slow rate of delivery, the fluid delivery system can be used to continuously deliver a fluid over a long period of time, e.g. 6 hrs, 12 hrs, 1 day, 3 days, 5 days, 10 days, one month, etc. The fluid delivery system comprises the hydraulic pump, coupled to a separate chamber for storing fluid to be delivered (the "fluid storage chamber" or "fluid chamber" in short). There could be various mechanisms coupling the movement of the barrier mechanism in the hydraulic pump to the fluid chamber, such that a small amount of fluid (ideally equal to, or at least proportional to the amount of the working fluid entering the hydraulic pump chamber) is expelled from the fluid chamber, through one or more orifice, in response to the movement of the barrier.

One embodiment of the fluid delivery system is illustrated in a high-level schematic drawing in FIG. 2 (see detailed description below). This type of fluid delivery system/device can be used for a broad range of applications, including but are not limited to biomedical research (e.g. microinjection into cells, nuclear or organelle transplantation, isolation of single cells or hybridomas, etc.), and clinical applications (administration of medicaments, etc.).

Figure 2:
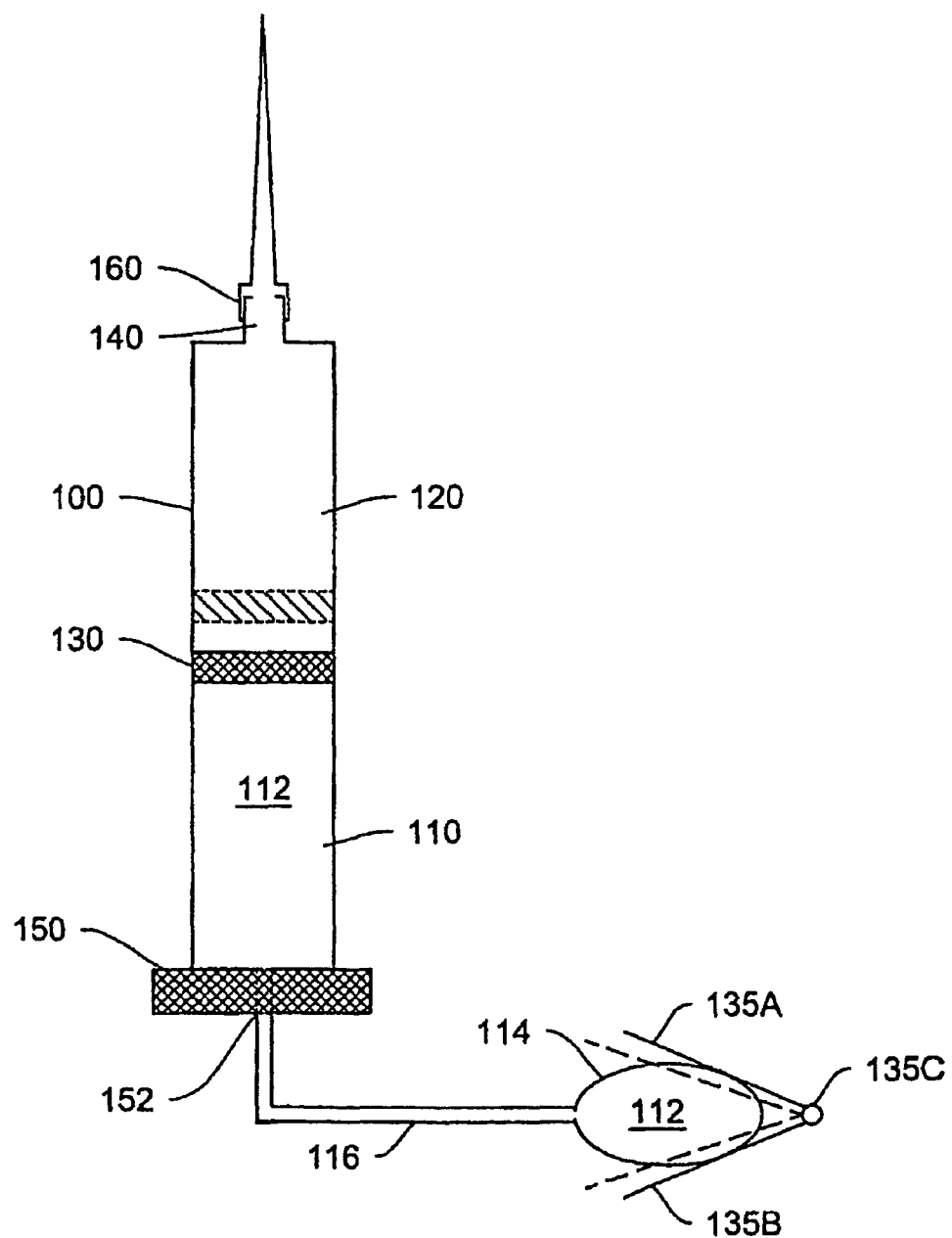
FIG. 2 is a high-level functional schematic drawing of a fluid delivery system comprising the hydraulic pump system, according to one embodiment of the invention.

Hydraulic cylinder 100, as described in FIG. 2, consists of two chambers, 110 and 120. Chamber 110 (corresponding to the pump chamber) is filled by hydraulic working fluid 112 from a hydraulic reservoir 114. Filling is accomplished by means of a connective passage 116, such as (but not limited to) a tube or lumen either flexibly or rigidly connecting hydraulic reservoir 114 and hydraulic cylinder 100. As hydraulic fluid 112 is forced out of reservoir 114 by actuator 135 (consisting, in an exemplary embodiment, of peristaltic compression plates 135A and 135B and hinge 135C), chamber 110 fills with hydraulic fluid expanding its volume and thus forcing piston element 130 (barrier mechanism) into chamber 120 (corresponding to the fluid chamber). The dotted lines in the actuator and the piston in FIG. 2 represent the later-in-time position of a plate-hinge actuating mechanism, and the later-in-time position of the barrier/piston.

Figure 3A:
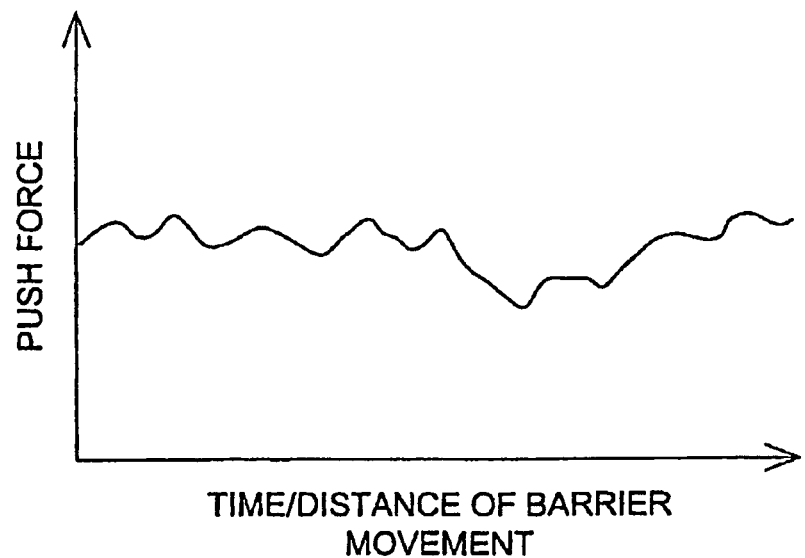
FIG. 3 is a schematic drawing illustrating one of the advantages of the fluid delivery system comprising the hydraulic pump system.
Figure 3B:
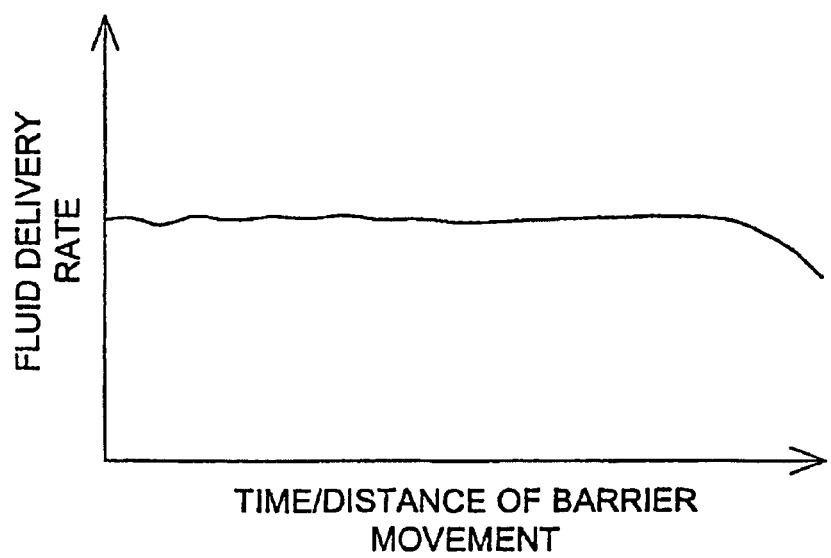
Figure 4A:
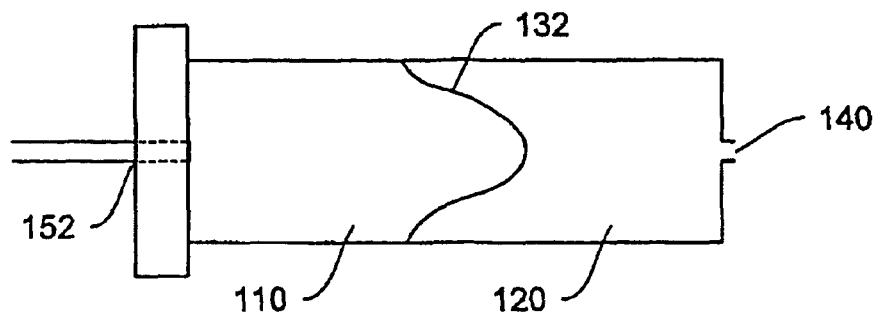
FIG. 4 is a high-level functional schematic drawing of several fluid delivery system with various barriers.
Figure 4B:
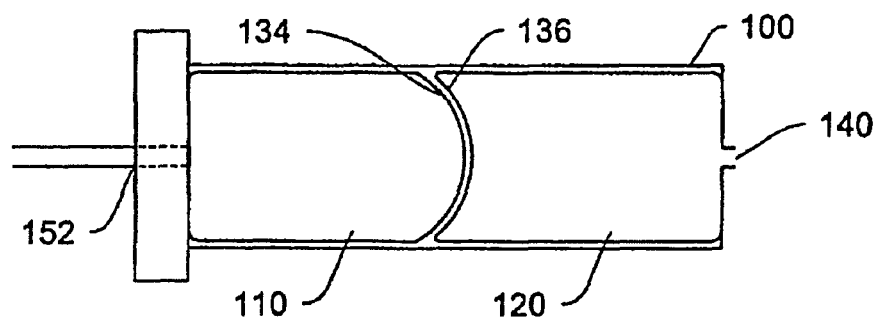
Figure 4C:
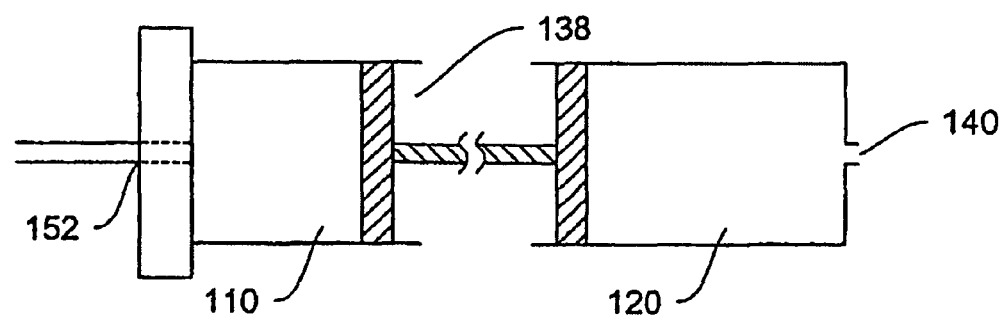

FIG. 3 is a schematic diagram illustrating one advantage of the fluid delivery system, e.g., its ability to tolerate relatively large variations in force generating the over-pressure, to create a relatively constant fluid delivery rate over time or distance traveled by the barrier piston. It is apparent that without the hydraulic pump system, any direct use of force to expel fluid in the fluid chamber will be hard to control, and will be subjected to a large variation in delivery rate of the fluid (FIG. 3A). In contrast, with the hydraulic pump, the delivery rate is much more constant (FIG. 3B).

FIGS. 4-8 describe various exemplary embodiments of the hydraulic pump-driven drug delivery system. The details of these pump embodiments are described in U.S.S.N. 60/465,070 (filed on Apr. 23, 2003, titled "HYDRAULICALLY ACTUATED PUMP FOR LONG DURATION MEDICAMENT ADMINISTRATION") and U.S. Pat. No. 7,530,968 (the entire contents incorporated herein by reference).

In its simplest embodiment, the hydraulic pump may form a portion of a single-use dispenser (e.g. syringe) for delivering GLP-1 through any of the standard, infusions sets available on the market today or likely to be available in the future. The pump, formed in some embodiments of low-cost plastic parts, may comprise a hydraulic cylinder containing two chambers. In those embodiments, the hydraulic cylinder may be configured similarly to most conventional hydraulic cylinders, and the wall, especially the inner wall of at least the chamber for storing a liquid medicament to be delivered, may be composed of bio-inert and inexpensive materials. The hydraulic cylinder typically consists of two chambers, one of which stores the medicament to be delivered (e.g. GLP-1 therapeutics), the other is filled with a high viscosity, ultra-pure hydraulic working fluid entered from a linked hydraulic reservoir through a connective passage. The hydraulic fluid is forced out of the reservoir by an actuator (consisting, in an exemplary embodiment, of peristaltic compression plates and a hinge), and enters the working fluid chamber through an extremely fine aperture with a diameter of about 2-3 µm. Because of the limited sized of the aperture, fluid enters the working fluid chamber at a slow, yet relatively consistent rate (such as about 100 nl-1 µl per minute, about 1-10 µl per minute, or about 10-100 μl per minute), which is relatively insensitive to other operation conditions, such as ambient temperature, pressure, etc. The working fluid enters the working fluid chamber, and displaces a barrier separating the working fluid chamber with the adjacent medicament chamber, causing a corresponding amount of GLP-1 medicament to exit through an orifice on the medicament chamber and into the connected infusion set mentioned above. The flow rate of the GLP-1 therapeutics can be controlled by the aperture size and the force generated by the actuator. Therefore, using this type of hydraulic pump, GLP-1 can be administered to a patient continuously to compensate for the constant degredation of the functional form of the GLP-1 therapeutics.

The dose of GLP-1, GLP-1 analog, or GLP-1 derivatives, or active fragments effective in a particular subject to cause desired effect (e.g. weight-loss) will depend on a number of factors, among which are included the subject's sex, weight and age, the underlying causes of disease or condition being treated, the route of administration and bioavailability, the persistence of the administered compound in the body, the formulation, and the potency. Where administration is intermittent, the dose per administration should also take into account the interval between doses, and the bioavailability of the administered compound. For weight-loss treatment, where administration is continuous, a suitable dosage rate is between 0.25 and 6 pmol/kg body weight/min, preferably from about 0.5 to about 1.2 pmol/kg/min, or from about 0.6 to about 2.4 pmol/kg/min. Typically, the maximum infusion rate can be controlled to no more than 2 pmol $kg^{-1}$ $min.^{-1}$ of GLP-1, since higher doses may be associated with the risk of side effects (Vilsboll et al., Diabetes Care 23: 807-812, 2000; Larsen et al., Diabetes Care 24: 1416-1421, 2001). It is within the skill of the ordinary physician to titrate the dose and rate of administration of compositions containing GLP-1, GLP-1 analogs, or GLP-1 derivatives, or active fragments thereof to achieve the desired clinical result.

Osmotic Pumps

In certain embodiments of the invention, GLP-1 therapeutics can be administered to a mammalian patient (including human or non-human animals) through the use of osmotic pumps. Elementary osmotic pumps are known in the art (see, e.g., Theeuwes, *Drug Dev. & Indust. Pharm.* 9: 1331-1357, 1983; Boudier, *Trends in Pharmacol. Sci.* pp. 162.164, April 1982, both of which are hereby incorporated by reference). These pumps were developed in response to the need to maintain the concentrations of drugs into a patient's plasma, particularly those that require chronic administration, within a safe and effective range. Conventionally, patients receive their medication by bolus administration (e.g., by injecting or otherwise administering a set amount of a drug). Immediately after such administration, the plasma level of the drug can exceed the maximum level for safety. But before the next scheduled administration, the level can fall below the minimum level required for effectiveness. As a result, patients are repeatedly exposed to both toxic and ineffective concentrations of drugs. The ratio of these two levels (the maximum level for safety and the minimum level for effectiveness) is known as the therapeutic index. While these fluctuations can be minimized by dosing at frequent time intervals, the required regimen can be extremely inconvenient for the patient (particularly where the drug has a short half-life). This is precisely the situation with GLP-1.

Examples of delivery systems in which osmotic pressure is the driving force behind drug release include PROGESTASERT7, a contraceptive system that releases progesterone to the uterine lumen at a rate of 65 microgram per day for one year, and OCUSERT7, an ocular system that releases pilocarpine to the eye at rates of 20 or 40 micrograms/hour for one week. Similarly, an elementary osmotic pump, such as described by Theeuwes (supra) can be used to dispense therapeutic agents into the gastrointestinal (GI) tract at a rate independent of external factors such as GI tract pH and motility. These systems illustrate two of the most prominent advantages of osmotic minipumps: constant and prolonged delivery of a drug at a predetermined rate and the ability to target delivery to a particular tissue or organ.

Structurally, osmotic pumps can include a solid core, semipermeable membrane and an orifice for drug delivery. Osmosis is the force driving expulsion of a drug from the device: water imbibed, e.g., from the environment, crosses the membrane at a controlled rate and causes the drug solution to exit through the delivery orifice. Delivery rate is controlled by osmotic properties of the core and membrane area, its thickness, and permeability to water.

WO0048669A1 (incorporated herein by reference) describes a type of osmotic pump relying on the change in the charge of the electroactive polymer within the pores of the device. This type of device can serve as a self-regulating osmotic pump, that might also be used to deliver GLP-1 into a patient. In this type of pump, charge neutralization can occur by migration of water and ions into and out of an electroactive polymer (i.e., by doping and undoping), thereby creating an osmotic pumping action.

When GLP-1 solution as a therapeutic agent is contained within that type of device and has access to the pores of the device (the GLP-1 therapeutic agent will be positioned so that it can move through the pores and into a patient's body), modulation of the diameter of the pore can, alone, be sufficient to allow sufficient movement of the therapeutic agent(s) into the outer electrolyte solution.

In another embodiment, the modulated current generated by charging the electroactive polymer in response to the level of analyte can be used to control an electromechanical pump that, when activated, forces the agent(s) through the open pore and into the outer electrolyte solution. Thus, in effect, the analyte level modulates both the pore opening and the pumping force. This double feed-back redundancy is an added safety feature of that type of system. If, for some reason, the pump failed to shut off at the appropriate time, the declining analyte concentration would cause the pore to close. When pressure within the reservoir containing the therapeutic agent(s) increases to a pre-set level, electrical contact to the pump is shut off until the pressure falls back to within its normal range of operation. If the pore fails to close as the analyte level falls (in response to infusion of the therapeutic agent(s)) the current generated by charging the electroactive polymer will also fall and the pump will gradually shut down.

If electron transfer between the GLP-1 therapeutic solution and the electroactive polymer is slower than between the member and the electroactive polymer, and if the applied potential across the polymer network is pulsed, then pulsing of the pore opening can also be achieved. During the "off" period, all or part of the polymer can be reduced or oxidized by the therapeutic agent so that the polymer returns to its virgin state. This opens the pore. The amount of charge transferred between pulses determines the size of the pore opening. When the potential is again turned on, the polymer is again fully charged and it closes. In effect, this on/off cycling can cause a pumping action. Thus, the pore size and the pumping action are modulated by the amount of analyte in the outer electrolyte solution. If a therapeutic agent was dissolved and stored on the inner side of the pore, pulsing of the pore could force the agent from inside the pore to the outer electrolyte solution. If the level of analyte was modulated by the amount of drug in the outer solution, the combination of the processes above would constitute a self-regulating drug delivery device. As in the case described above, pumping of the drug could be done through use of a conventional electromechanical pump.

In another embodiment, self-regulated pumping can be achieved by storing therapeutic agent(s) within a collapsible reservoir. As the pore open, the natural tendency would be for the drug to move from a solution of high concentration to a solution of low concentration until equilibrium is achieved. Modulation of the pore opening may also be used to regulate the amount of water imbibed by a collapsible reservoir surrounding the drug reservoir. Water imbibed when the pore is open causes the volume within the osmotic reservoir to increase, thereby forcing the therapeutic agent(s) out of the device.

The device itself can be used in a number of environments. It can be used in vivo or ex vivo (e.g., in a cell culture environment). In the event the device is used in vivo it may be wholly or partially internalized in a patient's body. For example, the device can include an adhesive component and a probe that extends beneath the body surface. When a portion of the device is worn externally, it can be attached to the patient by a belt, strap, or adhesive (e.g., it can be attached to the patient's skin by an adhesive patch). In some instances, an adhesive and a second security device (e.g., a belt or strap) can be used.

The amount of therapeutic agent carried within the device can vary. The amount can include less than 1, less than 2, less than 5 or less than 10 days supply of a therapeutic agent or agents.

Administration of Compositions

Administration may be via any route known to be effective by the physician of ordinary skill. Peripheral, parenteral administration is preferred. Parenteral administration is commonly understood in the medical literature as the injection of a dosage form into the body by a sterile syringe or the infusion pump described herein. Peripheral parenteral routes include intravenous, intramuscular, subcutaneous, and intraperitoneal routes of administration. Intravenous, intramuscular, and subcutaneous routes of administration of the compounds used in the present invention are more preferred. Intravenous and subcutaneous routes of administration of the compounds used in the present invention are yet more highly preferred. For parenteral administration, an active compound used in the present invention preferably is combined with distilled water at an appropriate pH. For human subjects, an active compound used in the present invention is combined with pyrogen-free distilled water at an appropriate pH, which meets FDA standard for human subject administration.

GLP-1 Analogs and Derivatives

Human GLP-1 amino acid sequence is described in numerous literatures, and is listed below:

GLP-1: 7, 8, 12, 16, 18, 19, 20, 22, 25, 27, 30, 33, and 37 (The entire teachings of these references are incorporated herein by reference). These novel GLP-1 analogs are extremely potent compared with ValB-GLP-1(7-37)OH. The increased potency of these analogs facilitates the use of delivery technology associated with limited bioavailability.

As used herein, "GLP-1 analogs" include GLP-1 compounds which are not natural GLP-1, but have sufficient homology to GLP-1(7-37)OH, GLP-1(7-36)NH$_2$ or a fragment of GLP-1(7-37)OH or GLP-1(7-36)NH$_2$, such that the analog has at least one biological function of GLP-1 (e.g., the ability to bind to a GLP-1 receptor, or insulinotropic activity, etc.). Preferably, a GLP-1 analog has the amino acid sequence of GLP-1(7-37)OH or a fragment thereof, modified so that from one, two, three, four, five, or six amino acids differ from the amino acid in the corresponding position of GLP-1(7-37) OH or a fragment of GLP-1(7-37)OH. In the nomenclature used herein to designate GLP-1 compounds, the substituting amino acid and its position is indicated prior to the parent structure.

A "GLP-1 derivative" is defined as a molecule having the amino acid sequence of GLP-1 or of a GLP-1 analog, but additionally having at least one chemical modification of one or more of its amino acid side groups, a-carbon atoms, terminal amino group, or terminal carboxylic acid group. A chemical modification includes adding chemical moieties, creating new bonds, and removing chemical moieties. Modifications at amino acid side groups include acylation of lysine ε-amino groups, N-alkylation of arginine, histidine, or lysine, alkylation of glutamic or aspartic carboxylic acid groups, and deamidation of glutamine or asparagine. Modifications of the terminal amino include the des-amino, N-lower alkyl, N-dilower alkyl, and N-acyl modifications. Modifications of the terminal carboxy group include the amide, lower alkyl amide, dialkyl amide, and lower alkyl ester modifications. A lower alkyl is a C1-C4 alkyl. Furthermore, one or more side groups, or terminal groups, may be protected by protective groups known to the ordinarily-skilled protein chemist. The a-carbon of an amino acid may be mono- or di-methylated.

Preferred GLP-1 analogs suitable for use in the instant invention include those described by formulae I and II of WO 03/018516 A2. Preferably, the GLP-1 analog compounds do not differ from GLP-1(7-37)OH or GLP-1(7-36)NH$_2$ by more than 6 amino acids, by more than 5 amino acids, by more than 4 amino acids, or by more than 3 amino acids. It is also preferable that the GLP-1 compounds of formulae I and II have valine or glycine at position 8 and glutamic acid at position 22. It is also preferable that the GLP-1 compounds of formulae I and II have valine or glycine at position 8 and glutamic acid at position 30. It is also preferable that the GLP-1 compounds of formulae I and II have valine or glycine at position 8 and histidine at position 37.

```
  1 mksiyfvagl fvmlvqgswq rslqdteeks rsfsasqadp lsdpdqmned krhsqgtfts
 61 dyskyldsrr aqdfvqwlmn tkrnrnniak rhdeferhae gtftsdvssy legqaakefi
121 awlvkgrgrr dfpeevaive elgrrhadgs fsdemntild nlaardfinw liqtkitdrk
```

See NCBI RefSeq NP_002045. Other alternative sequences from other mammals can be readily obtained from BLAST search of the nr database at NCBI or other public databases. All these sequences are incorporated herein by reference.

WO 03/018516 A2 describes various GLP-1 analogs with modifications at one or more of the following positions on The GLP-1 compounds described in WO 03/018516 A2 have increased potency compared to Val8-GLP-1(7-37) OH. Native GLP-1(7-37)OH is rapidly degraded by dipeptidylaminopeptidase IV (DPP-IV) after injection and the half-life of GLP-1(7-37)OH is approximately five minutes. Analogs such as Val8-GLP-1(7-37)OH wherein the alanine at position 8 has been substituted with a different amino acid have been developed because these analogs are resistant to DPP-IV degradation and thus, have an increased half-life. However, these analogs may not be potent enough to make administration by alternative delivery technology feasible on a commercial scale. Thus, Val8-GLP-1(7-37)OH is used as a comparator to illustrate the increased potency of the novel GLP-1 compounds encompassed in WO 03/018516 A2.

Preferably, the GLP-1 compounds described therein comprise GLP-1 analogs wherein the backbone for such analogs or fragments contains an amino acid other than alanine at position 8 (position 8 analogs). The backbone may also include L-histidine, D-histidine, or modified forms of histidine such as desamino-histidine, 2-amino-histidine, P-hydroxy-histidine, homohistidine, a-fluoromethylhistidine, or u-methyl-histidine at position 7. It is preferable that these position 8 analogs contain one or more additional changes at positions 12, 16, 18, 19, 20, 22, 25, 27, 30, 33, and 37 compared to the corresponding amino acid of native GLP-1(7-37)OH. It is more preferable that these position 8 analogs contain one or more additional changes at positions 16, 18, 22, 25 and 33 compared to the corresponding amino acid of native GLP-1(7-37)OH.

Furthermore, many of these more potent analogs have a reduced propensity to aggregate and thus, have increased stability. GLP-1 compounds can exist in at least two different forms. The first form is physiologically active and dissolves readily in aqueous solution at physiological pH (7.4). A second inactive form is readily produced when aqueous GLP-1 solutions are agitated, exposed to hydrophobic surfaces or have large air/water interfaces. The tendency to convert to the insoluble form considerably complicates the production of commercial quantities of active GLP-1 compounds. Thus, GLP-1 compounds that have a reduced propensity to aggregate in solution and are more potent than Val8-GLP-1(7-37)OH are preferred.

Numerous GLP-1 analogs and derivatives are also disclosed, to name but a few, in EP1408050A1, EP1100530A1, EP1368055A2, EP1306092A2, EP1187628A2, WO9111457A1, U.S. Pat. No. 5,545,618, DE69129226C0, EP0946191A1, EP0964692A1, EP0964873A1, U.S. Pat. No. 6,006,753, JP2001011095A2, U.S. Pat. No. 6,191,102, WO0135988A1, U.S. 20010011071A1, and U.S. Pat. No. 6,458,924. It is contemplated that other known GLP-1 analogs/derivatives already described in patent and other scientific literatures are all suitable to be administered using the pump technology of the invention.

In addition, novel heterologous GLP-1 fusion proteins comprises a GLP-1 compound fused to human albumin or to the Fc portion of an immunoglobulin are described in EP1355942A2 (Incorporated herein by reference.)

As used herein, the term "GLP-1 compound," including GLP-1, its fusion proteins, derivatives and analogs, also includes pharmaceutically acceptable salts of the compounds described herein. A GLP-1 compound can possess a sufficiently acidic, a sufficiently basic, or both functional groups, and accordingly react with any of a number of inorganic bases, and inorganic and organic acids, to form a salt.

The pharmaceutical composition can be a solution or, if administered parenterally, a suspension of the GLP-1 compound or a suspension of the GLP-1 compound complexed with a divalent metal cation such as zinc. Suitable pharmaceutical carriers may contain inert ingredients which do not interact with the GLP-1 peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Some examples of suitable excipients include lactose, dextrose, sucrose, trehalose, sorbitol, and mannitol.

A pharmaceutically-acceptable salt form of GLP-1, of a GLP-1 analog, or of a GLP-1 derivative may be used in the present invention. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. The salt forms are particularly preferred.

A GLP-1, GLP-1 analog, or GLP-1 derivative used in the present invention may be formulated with one or more excipients before use in the present invention. For example, the active compound used in the present invention may be complexed with a divalent metal cation by well-known methods. Such metal cations include, for example, $Zn^{++}$, $Mn^{++}$, $Fe^{++}$, $Co^{++}$, $Cd^{++}$, $Ni^{++}$, and the like.

The GLP-1 compounds may be formulated for administration such that blood plasma levels are maintained in the efficacious range for extended time periods. Various means can be employed to achieve a protracted time action including, for example, the incorporation of GLP-1 compounds into suspended amorphous or crystalline particles wherein the GLP-1 compound is complexed with zinc and slowly solubilizes upon administration. GLP-1 particles that provide a protracted action are described in EP 926 159 by Hoffmann et al. and EP 619 322 by Danley et al. In addition, depot formulations wherein a bioadsorbable polymer is used to provide sustained release over time are also suitable for use in the present invention.

Preparation of GLP-1 Analogs and Derivatives

Alterations to a precursor GLP-1 or GLP-1 amino acid sequence to produce a desired GLP-1 analog or GLP-1 derivative, or active fragment thereof, are made by well-known methods: solid-phase peptide synthesis techniques, chemical modification, enzymatic modification, or a combination of chemical and enzymatic modifications. The techniques of classical solution phase methods and semi-synthetic methods may also be useful for preparing the GLP-1 molecules used in the present invention. Methods for preparing the GLP-1 molecules of the present invention are well known to an ordinarily skilled peptide chemist. Peptide synthesizers are commercially available from, for example, Applied Biosystems in Foster City Calif. Reagents for solid phase synthesis are commercially available, for example, from Midwest Biotech is (Fishers, Ind.). Solid phase peptide synthesizers can be used according to manufacturers instructions for blocking interfering groups protecting the amino acid to be reacted, coupling, decoupling, and capping of unreacted amino acids. Identity of peptides can be verified by mass spectrometry. Peptides can be solubilized in aqueous buffers at neutral pH.

Addition of an acyl group to the epsilon amino group of Lys34 may be accomplished using any one of a variety of methods known in the art (Bioconjugate Chem. 1990; Hashimoto et al., 1989). For example, an N-hydroxy-succinimide ester of octanoic acid can be added to the lysyl-epsilon amine using 50% acetonitrile in borate buffer. The peptide can be acylated either before or after the imidazolic group is added. Moreover, if the peptide is prepared recombinantly, acylation prior to enzymatic cleavage is possible. Also, the lysine in the GLP-1 derivative can be acylated as taught in WO 96/29342.

The existence and preparation of a multitude of protected, unprotected, and partially-protected, natural and unnatural, functional analogs and derivatives of GLP-1 (7-36)amide and GLP-1 (7-37) molecules have been described (U.S. Pat. Nos. 5,120,712; 5,545,618 and 5,118,666; Orskov et al., 1989; WO 91/11457).

Optionally, the amino and carboxy terminal amino acid residues of GLP-1 derivatives may be protected, or, optionally, only one of the termini is protected. Reactions for the formation and removal of such protecting groups are described in works known to those of skill in the art including, for example, Protective Groups in Organic Chemistry 1973; Green, 1981; Schroder and Lübke, 1965. Representative amino-protecting groups include, for example, formyl, acetyl, isopropyl, butoxycarbonyl, fluorenylmethoxycarbonyl, carbobenzyloxy, and the like. Representative carboxy-protecting groups include, for example, benzyl ester, methyl ester, ethyl ester, t-butyl ester, p-nitro phenyl ester, and the like.

Carboxy-terminal, lower-alkyl-ester, GLP-1 derivatives used in the present invention are prepared by reacting the desired ($C_1$-$C_4$) alkanol with the desired polypeptide in the presence of a catalytic acid such as hydrochloric acid. Appropriate conditions for such alkyl ester formation include a reaction temperature of about 50° C. and reaction time of about 1 hour to about 3 hours. Similarly, alkyl ester derivatives of the Asp and/or Glu residues can be formed.

Preparation of a carboxamide derivative of a compound used in the present invention is formed, for example, as described in Stewart et al., 1984.

Exemplary Embodiments of Delivering GLP-1 and Analogs Thereof

The GLP-1 therapeutics, including GLP-1 and analogs thereof, may be delivered as medicaments to human or other non-human mammalian patients in various dosing schemes, depending on specific needs of the patients.

In certain embodiments, the medicament may be delivered in a constant rate, over a period spanning several hours, several days, several weeks, or even several months or years, so as to keep the concentration/amount of the medicament in vivo at a relatively constant level. For example, the fluid delivery system utilizing a hydraulic pump, as described in U.S. Ser. No. 60/465,070 and the related U.S. utility application U.S. Ser. No. 10/831,354, filed on Apr. 23, 2004, claiming priority to U.S. Ser. No. 60/465,070 (all incorporated herein be reference), may be employed for this purpose. The fluid delivery system takes advantage of a hydraulic pump, driven by a high-viscosity, ultrapure working fluid entering from a reservoir to a pump chamber through an extremely small aperture (about 1-100 µm in diameter) on the wall of the pump chamber, thus achieving slow, yet constant and smooth delivery of medicament stored in an adjacent storage chamber. As described therein, that type of device may be used to deliver potent medicaments such as GLP-1 and analogs thereof at a constant slow rate, over a long period of time (from several hours to days, weeks, or months).

In an alternative embodiment as described in U.S. Ser. No. 60/465,070 and the related utility application, a second reservoir that can be separately controlled can be attached to the pump chamber, either though the same or a different aperture (see FIG. 8). That separate reservoir may be used as a separate control mechanism to, for example, deliver an "on-demand boost" dose at predetermined intervals. Thus, when combined with the first reservoir, which delivers a constant dose of medicament, the second reservoir can be used to deliver a bolus of extra amount of medicament at times of need, such as after a meal, in additional to the low, constant level of medicament. In this embodiment, the boost does may be administered by the patient himself, or a qualified care provider, by simply activate the actuator attached to the second reservoir. For example, if the second actuator is a simple spring-plate mechanism held inactive by a barrier mechanism, as described in U.S. Ser. No. 60/465,070, it can be activated by temporarily removing a barrier mechanism by the patient or the care taker. After the boost administration, the barrier mechanism will be allowed to inactivate the second reservoir before the next boost administration.

In certain embodiments, medicaments may be delivered as doses that can be controlled through sensors and dose control indicator coupled to microneedles or microneedle arrays used to deliver the medicament. Several exemplary embodiments are described in detail in WO 03/024507 (incorporated herein be reference). Such devices contain a dose control system that selects or regulates a delivered dose based, at least in part, on a change in an electrical, magnetic or optical parameter. Briefly, the microneedle devices disclosed therein in some embodiments include a substrate; one or more microneedles; and, optionally, a reservoir for delivery of drugs or collection of analyte, as well as pump(s), sensor(s), and/or microprocessor(s) to control the interaction of the foregoing.

The pump-driven microneedle device may include a reservoir in communication with the pump and microneedles, so that fluid stored in the reservoir, when driven by the attached pump, may exit through the microneedles (or arrays/patches thereof). The reservoir can be attached to the substrate by any suitable means. In a preferred embodiment, the reservoir is attached to the back of the substrate (opposite the microneedles) around the periphery, using an adhesive agent (e.g., glue). A gasket may also be used to facilitate formation of a fluid-tight seal. In one embodiment, the reservoir contains drug (e.g. GLP-1 and analogs thereof), for delivery through the microneedles. The reservoir may be a hollow vessel, a porous matrix, or a solid form including drug which is transported therefrom. The reservoir can be formed from a variety of materials that are compatible with the drug or biological fluid contained therein. Preferred materials include natural and synthetic polymers, metals, ceramics, semiconductors, organics, and composites.

The microneedle device can include one or a plurality of chambers for storing materials to be delivered. In the embodiment having multiple chambers, each can be in fluid connection with all or a portion of the microneedles of the device array. In one embodiment, at least two chambers are used to separately contain drug (e.g., a lyophilized drug, such as a vaccine) and an administration vehicle (e.g., saline) in order to prevent or minimize degradation during storage. Immediately before use, the contents of the chambers may be mixed. Mixing can be triggered by any means, including, for example, mechanical disruption (i.c. puncturing or breaking), changing the porosity, or electrochemical degradation of the walls or membranes separating the chambers. In another embodiment, a single device is used to deliver different drugs, which are stored separately in different chambers. In this embodiment, the rate of delivery of each drug can be independently controlled.

In a preferred embodiment, the reservoir is in direct contact with the microneedles and have holes through which drug could exit the reservoir and now into the interior of hollow or porous microneedles. In another preferred embodiment, the reservoir has holes which permit the drug to transport out of the reservoir and onto the skin surface. From there, drug is transported into the skin, either through hollow or porous microneedles, along the sides of solid microneedles, or through pathways created by microneedles in the skin.

The pump-driven microneedle device described therein is capable of transporting material across the barrier (e.g. skin) at a useful rate, e.g., a rate sufficient to be therapeutically useful. The device may include a housing with microelectronics and other micromachined structures to control the rate of delivery either according to a preprogrammed schedule or through active interface with the patient, a healthcare professional, or a biosensor. The rate can be controlled by manipulating a variety of factors, including the characteristics of the drug formulation to be delivered (e.g., its viscosity, electric charge, and chemical composition); the dimensions of each microneedle (e.g., its outer diameter and the area of porous or hollow openings); the number of microneedles in the device; the application of a driving force (e.g., a concentration gradient, a voltage gradient, a pressure gradient); and the use of a valve.

The rate also can be controlled by interposing between the drug in the reservoir and the opening(s) at the base end of the microneedle polymeric or other materials selected for their diffusion characteristics. For example, the material composition and layer thickness can be manipulated using methods known in the art to vary the rate of diffusion of the drug of interest through the material, thereby controlling the rate at which the drug flows from the reservoir through the microneedle and into the tissue.

Transportation of molecules through the micioneedles can be controlled or monitored using, for example, various combinations of valves, pumps, sensors, loactuators, and microprocessors. These components can be produced using standard manufacturing or microfabrication techniques. Actuators that may be useful with the microneedle devices disclosed herein include micropumps, microvalves, and positioners. In a preferred embodiment, a microprocessor is programmed to control a pump or valve, thereby controlling the rate of delivery.

Flow of molecules through the microneedles can usually occur based on diffusion, capillary action, or can be induced using mechanical pumps (conventional or the subject hydraulic pump, one of a preferred embodiments) or non-mechanical driving forces, such as electroosmosis or electrophoresis, or convection. For example, in electroosmosis, electrodes are positioned on the biological barrier surface, one or more microneedles, and/or the substrate adjacent the needles, to create a convective flow which carries oppositely charged ionic species and/or neutral molecules toward or into the biological barrier. In a preferred embodiment, the microneedle device is used in combination with another mechanism that enhances the permeability of the biological barrier, for example by increasing cell uptake or membrane disruption, using electric fields, ultrasound, chemical enhancers, viruses, pH, heat and/or light.

Passage of the microneedles, or drug to be transported via the microneedles, can be manipulated by shaping the microneedle surface, or by selection of the material forming the microneedle surface (which could be a coating rather than the microneedle per se). For example, one or more grooves on the outside surface of the microneedles can be used to direct the passage of drug, particularly in a liquid state.

Alternatively, the physical surface properties of the microneedle could be manipulated to either promote or inhibit transport of material along the microneedle surface, such as by controlling hydrophilicity or hydrophobicity.

The flow of molecules can be regulated using a wide range of valves or gates. These valves can be the type that are selectively and repeatedly opened and closed, or they can be single-use types. For example, in a disposable, single-use drug delivery device, a fracturable barrier or one-way gate may be installed in the device between the reservoir and the opening of the microneedles. When ready to use, the barrier can be broken or gate opened to permit flow through the microneedles. Other valves or gates used in the microneedle devices can be activated thermally, electrochemically, mechanically, or magnetically to selectively initiate, modulate, or stop the flow of molecules through the needles. In a preferred embodiment, flow is controlled by using a rate-limiting membrane as a "valve." The microneedle devices can further include a flowmeter or other dose control system to monitor flow and optionally control flow through the microneedles and to coordinate use of the pumps and valves.

Useful sensors may include sensors of pressure, temperature, chemicals, and/or electromagnetic fields. Biosensors can be employed, and in one arrangement, are located on the microneedle surface, inside a hollow or porous microneedle, or inside a device in communication with the body tissue via the microneedle (solid, hollow, or porous). These microneedle biosensors may include any suitable transducers, including but not limited to potentionietric, amperometric, optical, magnetic and physiochemical. An amperometric sensor monitors currents generated when electrons are exchanged between a biological system and an electrode. Blood glucose sensors frequently are of this type, and is particularly useful for controlling the administration of GLP-1 and its functional analogs. As described herein, the sensors may be formed to sense changes resulting from an election transfer agent interacting with analyte or analytes of interest, e.g. blood glucose level.

The microneedle may function as a conduit for fluids, solutes, electric charge, light, or other materials. In one embodiment, hollow microneedles can be filled with a substance, such as a gel, that has a sensing functionality associated with it. In an application for sensing based on binding to a substrate or reaction mediated by an enzyme, the substrate or enzyme can be immobilized in the needle interior, which would be especially useful in a porous needle to create an integral needle/sensor.

Wave guides can be incorporated into the microneedle device to direct light to a specific location, or for dection, for example, using means such as a pH dye for color evaluation. Similarly, heat, electricity, light or other energy forms may be precisely transmitted to directly stimulate, damage, or heal a specific tissue or intermediary (e.g., tattoo remove for dark skinned persons), or diagnostic purposes, such as measurement of blood glucose based on IR spectra or by chromatographic means, measuring a color change in the presence of immobilized glucose oxidase in combination with an appropriate substrate.

In a preferred embodiment, the microneedle device includes an adhesive to temporarily secure the device to the surface of the biological barrier. The adhesive can be essentially anywhere on the device to facilitate contact with the biological barrier. For example, the adhesive can be on the surface of the collar (same side as microneedles), on the surface of the substrate between the microneedles (near the base of the microneedles), or a combination thereof.

Pages 13-18 of the published PCT WO 03/024507 describes in detail the different embodiments of the microneedles and arrays thereof that may be coupled to the subject fluid delivery system. The contents are incorporated herein by reference.

Methods of manufacturing, as well as various design features and methods of using, the microneedles and microneedle arrays described herein are disclosed, for example, in Published PCT patent application WO 99/64580, entitled "Microneedle Devices and Methods of Manufacture and Use Thereof," Published PCT patent application WO 00/74763, entitled "Devices and Methods for Enhanced Microneedle Penetration or Biological Barriers," Published PCT patent application WO 01/49346, and published PCT WO 00/48669, each of which is incorporated herein by reference. Generally, the microneedles and arrays thereof can be prepared using a variety of ways, including electrochemical etching techniques, plasma etching techniques, electroplating techniques, and microfabrication techniques.

Figure 5:
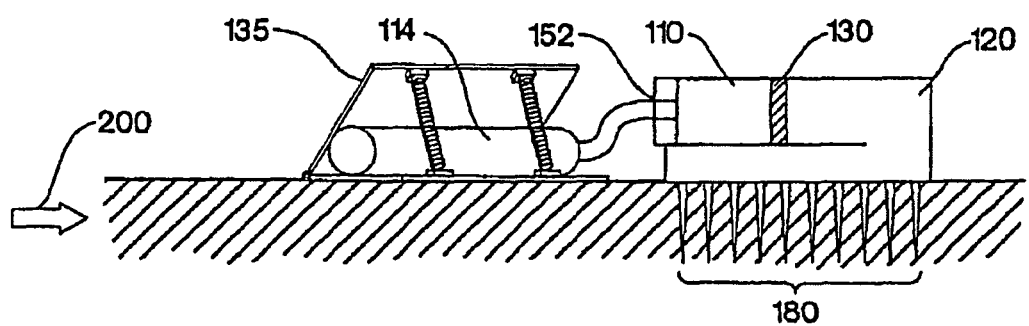
FIG. 5 is a high-level functional schematic drawing of an alternative fluid delivery system, according to one embodiment of the invention. The alternative fluid delivery system in this embodiment features arrayed microneedles on an transdermal patch.
Figure 6A:
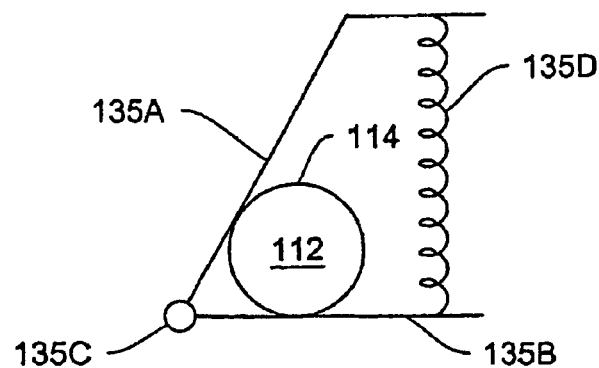
FIG. 6 is a high-level functional schematic drawing of several actuator mechanisms that can be used with the fluid delivery system employing the hydraulic pump, according to one embodiment of the invention.
Figure 6B:
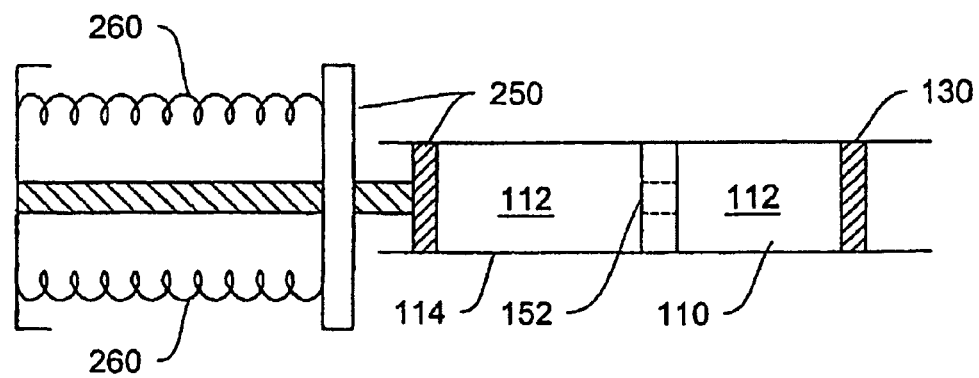
Figure 6C:
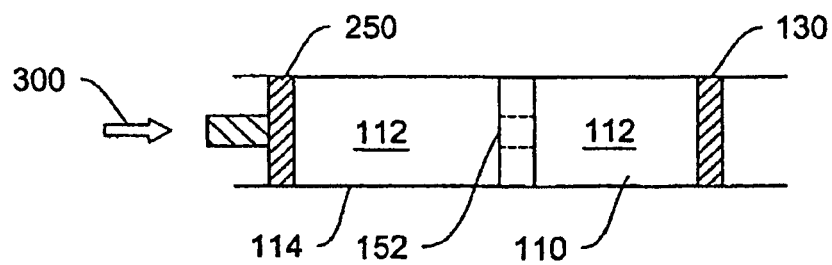
Figure 7:
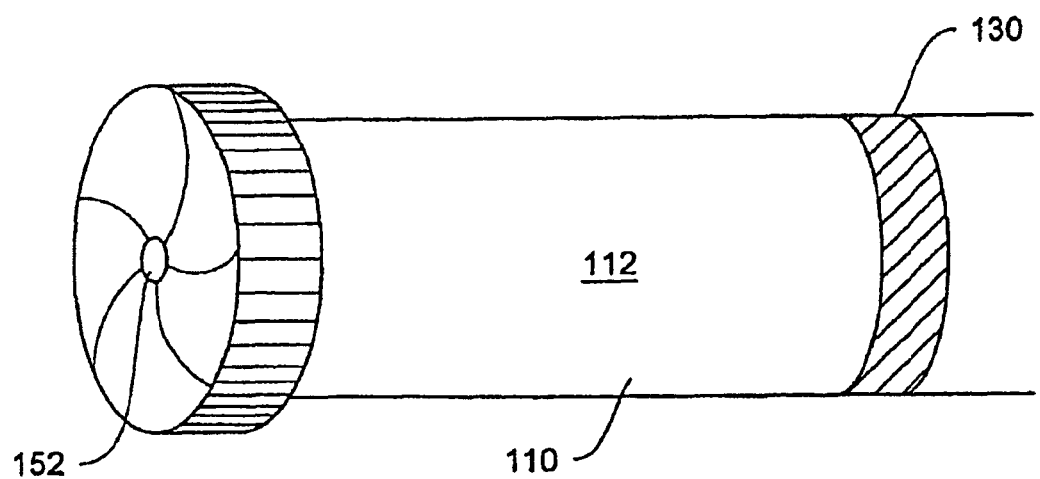
FIG. 7 is a high-level functional schematic drawing of the adjustable control for aperture opening size.
Figure 8A:
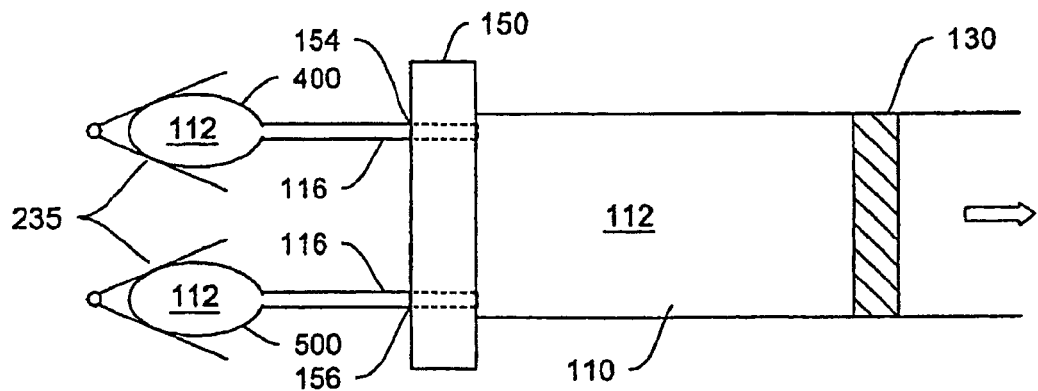
FIG. 8 is a high-level functional schematic drawing of several fluid delivery system with multiple actuators, according to one embodiment of the invention.
Figure 8B:
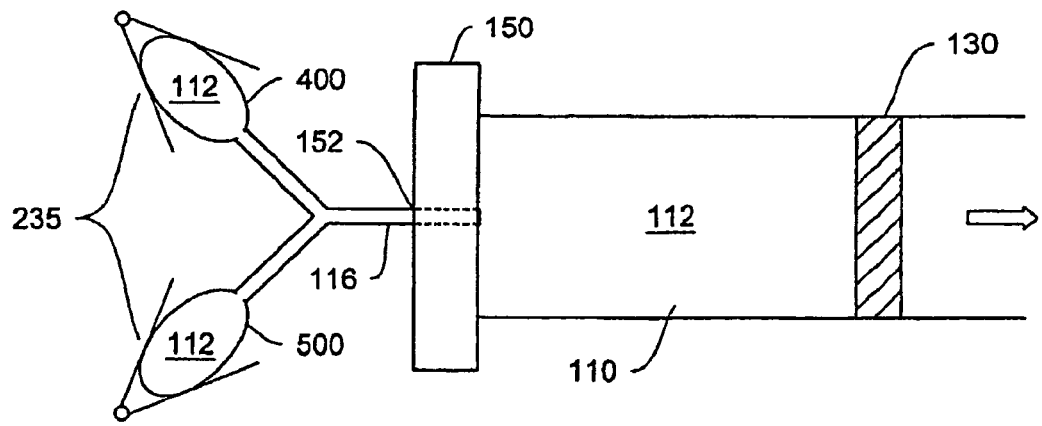
Figure 9:
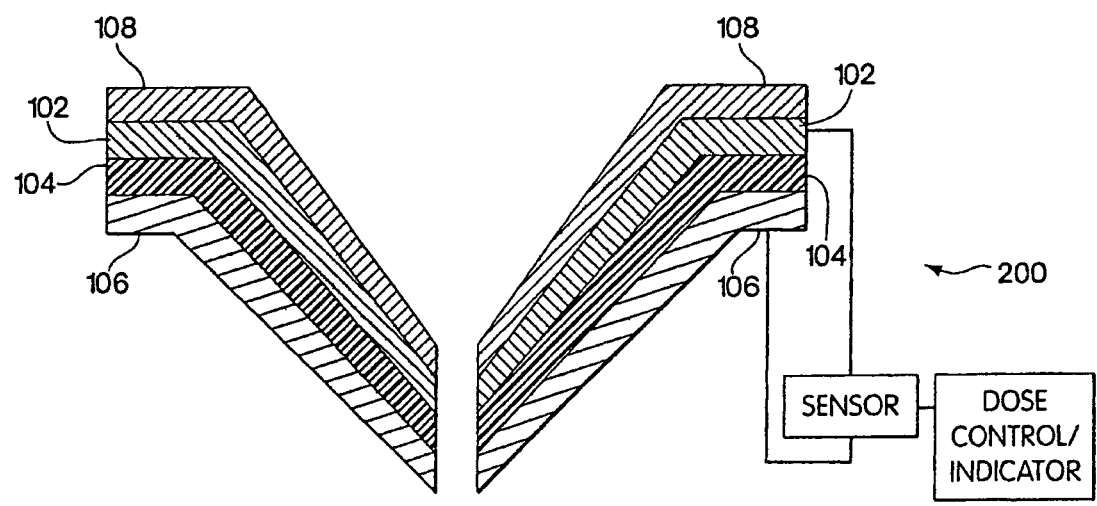
FIG. 9 depicts one embodiment of a microneedle coupled to the subject fluid delivery system, which employs a sensor for detecting the presence of one or more analytes and control delivery rate.

FIG. 9 depicts the microneedle 200 with a sensor electrically coupled between the metal layer 102 and the metal layer 106. The sensor can be suitable sensor capable of measuring or detecting a change in an electrical parameter, such as voltage, current, capacitance, resistance and/or inductance. The sensor may comprise a resistor, differential amplifier, capacitance meter or any other suitable device. In the embodiment of FIG. 5, the sensor measures changes in an electrical parameter, but is other embodiments, the sensor may be capable of measuring a magnetic parameter, such as a hall effect device, or an optical, characteristic. The sensor may generate a signed capable of operating a dose control system or flow meter that controls or allows the flow of a drug to the patient.

Optionally, the sensor may control an alarm or indicator that may be visual, or auditory.

In embodiments, microneedles, microneedle arrays, and/or microneedle systems can be involved in delivering drugs. For example, a system can include a sample section and a delivery section. The sections can be in communication so that the delivery section delivers one or more desired medicaments in response to a signal from the sample section.

The device may be used for single or multiple uses for rapid transport across a biological barrier or may be left in place for longer times (e.g., hours or days) for long-term transport of molecules. Depending on the dimensions of the device, the application site, and the route in which the device is introduced into (or onto) the biological barrier, the device may be used to introduce or remove molecules at specific locations.

In one embodiment, the microneedle device may be used in a transdermal application to deliver GLP-1 or analogs. The device is applied to the skin such that the microneedles penetrate through the stratum corneum and enter the viable epidermis so that the tip of the microneedle at least penetrates into the viable epidermis. In a preferred embodiment, drug molecules in a reservoir within the upper portion flow through or around the microneedles and into the viable epidermis, where the drug molecules then diffuse into the dermis for local treatment or for transport through the body.

To control the transport of material out of or into the device through the microneedles, a variety of forces or mechanisms can be employed. These include pressure gradients, concentration gradients, electricity, ultrasound, receptor binding, heat, chemicals, and chemical reactions. Mechanical or other gates in conjunction with the forces and mechanisms described above can be used to selectively control transport of the material.

In particular embodiments, the device should be "user-friendly." For example, in some transdermal applications, affixing the device to the skin should be relatively simple, and not require special skills. This embodiment of a microneedle may include an array of microneedles attached to a housing containing drug in an internal reservoir, wherein the housing has a bioadhesive coating around the microneedles. The patient can remove a peel-away backing to expose an adhesive coating, and then press the device onto a clean part of the skin, leaving it to administer drug over the course of, for example, several days.

In this way, many drugs can be delivered at a variety of therapeutic rates. The rate can be controlled by varying a number of design factors, including the outer diameter of the microneedle, the number and size of pores or channels in each microneedle, the number of microneedles in an array, the magnitude and frequency of application of the force driving the drug through the microneedle and/or the holes created by the microneedles. For example, devices designed to deliver drug at different rates might have more microneedles for more rapid delivery and fewer microneedles for less rapid delivery. As another example, a device designed to deliver drug at a variable rate could vary the driving force (e.g., pressure gradient controlled by a pump) for transport according to a schedule which was preprogrammed or controlled by, for example, the user or his doctor. The devices can be affixed to the skin or other tissue to deliver drugs continuously or intermittently, for durations ranging from a few seconds to several hours or days.

One of skill in the art can measure the rate of drug delivery for particular microneedle devices using in vitro and in vivo methods known in the art. For example, to measure the rate of transdermal drug delivery, human cadaver skin mounted on standard diffusion chambers can be used to predict actual rates. See Hadgraft & Guy, eds., Transdermal Drug Delivery: Developmental Issues and Research Initiatives (Marcel Dekker, New York 1989); Bronaugh & Maibach, Percutaneous Absorption, Mechanisms—Methodology—Drug Delivery (Marcel Dekker, New York 1989). After filling the compartment on the dermis side of the diffusion chamber with saline, a microneedle array is inserted into the stratum corneum; a drug solution is placed in the reservoir of the microneedle device; and samples of the saline solution are taken over time and assayed to determine the rates of drug transport.

Exemplary Therapeutic Uses of GLP-1

GLP-1 compounds encompassed by the present invention exert their biological effects by acting at a receptor referred to as the "GLP-1 receptor" (see U.S. Pat. No. 5,670,360). Subjects with diseases and/or conditions that respond favorably to GLP-1 receptor stimulation or to the administration of GLP-1 compounds can therefore be treated with the GLP-1 compounds of the present invention. These subjects are said to "be in need-of treatment with GLP-1 compounds" or "in need of GLP-1 receptor stimulation."

Included are subjects with non-insulin dependent diabetes, insulin dependent diabetes, stroke (see WO 00/16797 by Efendic), myocardial infarction (see WO 98/08531 by Efendic), obesity (see WO 98/19698 by Efendic), catabolic changes after surgery (see U.S. Pat. No. 6,006,753 to Efendic), functional dyspepsia and irritable bowel syndrome (see WO 99/64060 by Efendic). Also included are subjects requiring prophylactic treatment with a GLP-1 compound, e.g., subjects at risk for developing non-insulin dependent diabetes (see WO 00/07617). Additional subjects include those with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

The GLP-1 compounds can be used to normalize blood glucose levels, prevent pancreatic P-cell deterioration, induce P-cell proliferation, stimulate insulin gene transcription, up-regulate IDX-I/PDX-1 or other growth factors, improve P-cell function, activate dormant cells, differentiate cells into P-cells, stimulate P-cell replication, inhibit P-cell apoptosis, regulate body weight, and induce weight loss.

An "effective amount" of a GLP-1 compound is the quantity which results in a desired therapeutic and/or prophylactic effect without causing unacceptable side effects when administered to a subject in need of GLP-1 receptor stimulation. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a GLP-1 compound for the treatment of diabetes is the quantity that would result in greater control of blood glucose concentration than in the absence of treatment, thereby resulting in a delay in the onset of diabetic complications such as retinopathy, neuropathy or kidney disease. An "effective amount" of a GLP-1 compound for the prevention of diabetes is the quantity that would delay, compared with the absence of treatment, the onset of elevated blood glucose levels that require treatment with anti-hypoglycaemic drugs such as sulfonyl ureas, thiazolidinediones, insulin and/or bisguanidines.

An "effective amount" of the GLP-1 compound administered to a subject will also depend on the type and severity of the disease and on the characteristics of the subject, such as general health, age, sex, body weight and tolerance to drugs. Typically, the GLP-1 compounds of the present invention will be administered such that plasma levels are within the range of about 5 picomoles/liter and about 200 picomoles/liter. Optimum plasma levels for Val8GLP-1(7-37)OH were determined to be between 30 picomoles/liter and about 200 picomoles/liter. Because some of the GLP-1 analogs are more potent than Val8-GLP-1 (7-37) OH, the optimum plasma levels will be lower. Generally, a GLP-1 compound that has an in vitro or in vivo potency that is 3-fold better than Val8-GLP-1(737)OH will be administered such that plasma levels are 3-fold lower than the optimum levels determined for Val8-GLP1(7-37)OH.

A typical dose range for the GLP-1 compounds will range from about 0.01 mg per day to about 1000 mg per day for an adult. Preferably, the dosage ranges from about 0.1 mg per day to about 100 mg per day, more preferably from about 1.0 mg/day to about 10 mg/day.

A "subject" or a "patient" is a mammal, preferably a human, but can also be an animal, e.g., companion animals (e.g., dogs, cats, and the like), farm animals (e.g., cows, sheep, pigs, horses, and the like) and laboratory animals (e.g., rats, mice, guinea pigs, and the like).

The following section describes in detail various biological effects of GLP-1 and analogs thereof. In many cases, these effect of GLP-1 can be effectuated by infusion of GLP-1, either continuously, or intermittently, using the various pump devices described above to achieve predetermined infusion rates and patterns.

The biological activities of GLP-1 include stimulation of glucose-dependent insulin secretion and insulin biosynthesis, inhibition of glucagon secretion and gastric emptying, and inhibition of food intake. GLP-1 appears to have a number of additional effects in the GI tract and central nervous system (CNS), as reviewed in Diabetes 1998 47(2):159-69; Drucker, Endocrinology 142(2): 521-7, 2001; Drucker, Curr Pharm Des. 7(14): 1399-412, 2001; Drucker, Gastroenterology 122 (2): 531-44, 2002. These include strong inhibition of gastro-pancreatic secretion and gastric motility (O'Halloran et al., J. Endocrinol. 126: 169-173, 1990; Schjoldager et al., Dig. Dis. Sci. 34: 703-708, 1989; Wettergren et al., Scand. J. Gastroenterol. 32: 552-555, 1997; Wettergren et al., Scand. J. Gastroenterol. 29: 501-505, 1994; Wettergren et al., Dig. Dis. Sci. 4: 665-673, 1993), and mediating the ileal-brake effect (i.e., the endocrine inhibition of upper gastrointestinal motility and secretion elicited by the presence of nutrients in the distal small intestine; Layer et al., Dig. Dis. Sci. 40: 1074-1082, 1995).

GLP-1 and the β Cell

One of the first actions identified for GLP-1 was the glucose-dependent stimulation of insulin secretion from islets in rodents, humans, or from islet cell lines. See Mojsov et al., J. Clin. Invest. 79(2): 616-9, 1987; Kreymann et al., Lancet 2(8571): 1300-4, 1987; Holst et al., FEBS Lett. 211(2): 169-74, 1987; and Drucker et al., PNAS USA. 84(10): 3434-8, 1987. Following the detection of GLP-1 receptors on islet beta cells, a large body of evidence has accumulated illustrating that GLP-1 exerts multiple actions on various signaling pathways and gene products in the β cell. For a summary of β cell genes and proteins activated by GLP-1, see table below.

| Summary of β Cell genes and proteins activated by GLP-1 | |
|---|---|
| Experimental Model | Gene or Protein |
| INS-1 cells | Akt and IRS proteins |
| INS-1 cells | Glucokinase |
| RIN1046-38 cells | GLUT-1 RNA |
| RIN1046-38 cells | Hexokinase I RNA |
| INS-1 cells | Immediate early genes |
| Multiple cell models | Insulin RNA |
| INS-1 cells | Kir 6.2 RNA |
| Multiple islet cell lines | Pdx-1 RNA and protein |
| RIN1046-38 cells | SNAP-25 phosphorylation |
| INS-1 cells | Calcineurin and NFAT |

GLP-1, Islet Proliferation and Differentiation And Apoptosis

The finding that GLP-1 lowers blood glucose in patients with diabetes, taken together with suggestions that GLP-1 may restore β cell sensitivity to exogenous secretagogues, suggests that augmenting GLP-1 signaling is a useful strategy for treatment of diabetic patients. There are a number of different GLP-1 targets or loci that may be exploited to enhance GLP-1 action in diabetic subjects.

Mounting evidence also strongly suggests that GLP-1 signaling regulates islet proliferation and islet neogenesis. The observations that GLP-1R agonists including exendin-4 may play a role in islet neogenesis or differentiation have engendered considerable interest and excitement given the potential of these actions to enhance b cell function in subjects with Type 2 diabetes. Furthermore, the possibility that GLP-1 receptor activation may enhance β cell mass in patients with Type 1 diabetes is also under active investigation, in a NIH sponsored clinical trial (Effect of AC2993 with or without Immunosuppression on Beta Cell Function in Patients with Type I Diabetes, Sponsored by National Institute of Diabetes and Digestive and Kidney Diseases (NIDDK)).

Complementary findings from several labs, using a variety of experimental rodent and cell models, indicate that GLP-1 agonists may modulate β cell mass in part via reduction of P cell apoptosis. These actions may be directly relevant to protection of human islet P cells as incubation of human islets with native GLP-1 for 5 days preserved islet morphology, reduced the expression of pro-apoptotic genes, decreased cell death, and improved glucose-stimulated insulin secretion. See Farilla et al., Endocrinology 144(12): 5149-58, 2003; Drucker, Endocrinology 144(12): 5145-5148, 2003.

The anti-apoptotic properties of GLP-1 agonists have been demonstrated in Zucker diabetic rats and db/db mice. A 2 day infusion of GLP-1 increased islet size and β cell mass, and reduced the numbers of apoptotic cells in the exocrine portion of the pancreas. The percentage of apoptotic β cells in this study was surprisingly high at greater than 20%, and was significantly reduced by GLP-1 treatment. See Farilla et al., Endocrinology 143(11): 4397-4408, 2002.

Treatment of normoglycemic db/db mice with daily exendin-4 for 14 days prevented the progression to more frank diabetes, increased β cell mass, and numbers of BrdU+islet cells, and reduced numbers of Tunel+apoptotic β cells. Exendin-4-treated rats also exhibited increased levels of pancreatic Akt1, the prosurvival kinase, increased p44 MAP kinase, and reduced expression of activated caspase-3. See Wang and Brubaker, Diabetologia 45(9): 1263-73, 2002.

Similarly, treatment of mice with exendin-4 reduced β cell apoptosis induced by streptozotocin (STZ), whereas GLP-1R−/− mice exhibited increased susceptibility to STZ-induced β cell apoptosis. Furthermore, exendin-4 directly reduced the extent of apoptotic cell death in purified rat b cells exposed to a combination of cytotoxic cytokines, and GLP-1 or exendin-4 increased cell survival and reduced caspase activation in BHK fibroblasts expressing a transfected GLP-1 receptor. Hence these findings implicate a direct role for β cell GLP-1 receptor signaling in regulation of the resistance to cellular apoptosis. See Li et al., J. Biol. Chem. 278(1): 471-8, 2003.

Treatment of Min6 mouse islet cells with GLP-1 reduced the extent of hydrogen peroxide-induced apoptosis in vitro. The anti-apoptotic effects of GLP-1 were partially blocked by either the cAMP "antagonist" Rp-cAMP, or the PI 3-kinase inhibitor LY294002. GLP-1 prevented cell death only when applied prior to exposure of cells to peroxide. See Hui et al., Endocrinology 144(4): 1444-55, 2003.

Similarly, induction of fatty acid induced apoptosis in Rinm5F cells with palmitate was markedly reduced by agents that increased levels of cyclic AMP, including Cyclic AMP dose-dependently prevents palmitate-induced apoptosis by both PKA- and cAMP-GEF-dependent pathways in beta-cells. Kwon et al., J. Biol. Chem. 279(10): 8938-45, 2004 (Epub 2003 December 19).

Related studies using rat INS-1 cells demonstrated that protein kinase B (Akt) is rapidly activated by Glucagon-like peptide-1 regulates proliferation and apoptosis via activation of protein kinase B in pancreatic INS-1 beta cells. Wang et al., Diabetologia 47(3): 478-87, 2004 (Epub 2004 Feb 05).

The anti-apoptotic actions of GLP-1 agonists have been demonstrated in cultured fetal rat hippocampal neurons which exhibit GLP-1-dependent increases in cAMP formation. Both GLP-1 and exendin-4 significantly reduced the extent of glutamate-induced cell death in short term cultures of hippocampal neurons. Furthermore, both GLP-1 and exendin-4 reduced depletion of choline acetyltransferase immunoreactivity, a marker for cholinergic neurons in the basal forebrain, following administration of ibotenic acid. See Perry et al., J. Pharmacol. Exp. Ther. 302(3): 881-8, 2002; Gilman et al., J. Neurochem. 87(5): 1137-44, 2003.

The calpain-10 molecule has also been linked to β cell apoptosis, and may be modified by GLP-1 receptor activation. GLP-1 decreased calpain activity, reversed ryanodine-induced calpain activation and apoptosis in β cells and MIN6 cells, as shown in RyR2 and calpain-10 delineate a novel apoptosis pathway in pancreatic islets. Johnson et al., J. Biol. Chem. 2004 Mar 25 [Epub ahead of print].

Evidence that GLP-1 stimulates islet cell proliferation in vitro is illustrated in Glucose and glucoincretin peptides synergize to induce c-fos, c-jun, junB, zif-268, and nur-77 gene expression in pancreatic beta(INS-1) cells. Susini et al., FASEB J. 12(12): 1173-82, 1998; Buteau et al., Diabetologia 42(7): 856-64, 1999.

The signal transduction system activated by the GLP-1R signaling system depends on the islet cell model under study, with cAMP, PKC and PI-3-kinase activated by the GLP-1R in several studies. Buteau et al., Diabetes 50(10): 2237-2243, 2001.

Provocative experiments using the INS-1 cell line demonstrate the potential involvement of the EGFR and EGFR ligands such as betacellulin in the direct and indirect GLP-1R-dependent activation of cell proliferation as shown in Glucagon-Like Peptide 1 Induces Pancreatic beta-Cell Proliferation Via Transactivation of the Epidermal Growth Factor Receptor. Buteau et al., Diabetes 52(1): 124-32, 2003.

The cyclic AMP-dependent transcription factor CREB has been linked to GLP-1-mediated cell growth and survival, as outlined in cAMP promotes pancreatic beta-cell survival via CREB-mediated induction of IRS2. Jhala et al., Genes Dev. 17(13): 1575-80, 2003.

Incubation of pancreatic exocrine cells with GLP-1 or exendin-4 promotes differentiation of the AR42J cell line to an endocrine phenotype. Differentiated cells exhibited increased expression of β cell genes and the capacity for glucose-dependent insulin secretion. Zhou et al., Diabetes 48(12): 2358-66, 1999.

Similarly, treatment of fetal (75-90 day gestational age) pig islet clusters with GLP-1 promoted glucose-dependent insulin secretion and after several days of treatment with GLP-1R agonists, the cells exhibited increased Pdx-1 expression and enhanced differentiation along the β cell pathway. Furthermore, transplantation of the GLP-1-treated islet clusters into SCID mice revealed a significantly increased number of functionally mature β cells after 8 weeks in vivo. See Hardikar et al., Endocrinologyl 43(9):3505-14, 2002.

GLP-1(1-37) also plays a role in intestinal differentiation. The vast majority of GLP-1 produced in gut endocrine cells is either GLP-1(7-36)amide or GLP-1(7-37). Very little is known about the generation and biological activity of GLP-1(1-37). Suzuki et al. demonstrate that GLP-1(1-37) is capable of inducing intestinal cells to undergo β cell-like differentiation, in association with development of glucose-dependent insulin secretion. These effects were observed using organ culture in vitro, blocked by the GLP-1R antagonist exendin(9-39) and were also detected following injection of pregnant or adult mice with GLP-1(1-37) in vivo. See Suzuki et al., Proc. Natl. Acad. Sci. U.S.A. 100(9): 5034-9, 2003 (Epub 2003 Apr 17).

GLP-1 is further implicated in human β cell differentiation. A series of elegant experiments now demonstrates that a combination of GLP-1 receptor agonists (such as exendin-4), pdx-1 expression, and cell-cell contact, promotes the development of a more differentiated P cell in vitro. See de la Tour et al., Mol. Endocrinol. 15(3): 476-483, 2001. Similarly, incubation of the human ductal cell line Capan-1, which expresses the GLP-1R, with exendin-4 results in a significant increase in the number of cells exhibiting immunopositivity for insulin or glucagon, and induction of islet genes such as PDX-1, BETA2/NeuroD, and HNF-3b. Increased binding of HNF-3b to Pdx-1 promoter elements may represent one component of the differentiation mechanism activated by the GLP-1R in these cells. See Zhou et al., J. Cell. Physiol. 192(3): 304-14, 2002.

GLP-1R (receptor for GLP-1) has also been localized to nestin positive islet-derived progenitor cells (NIPs) identified in islets and duct cells. About 60% of NIPs exhibit GLP-1R immunopositivity, and the GLP-IR is capable of transducing a functional $[Ca^{2+}]i$ response that is blocked by the GLP-1R antagonist exendin(9-39); this response was detected at normal but not elevated glucose concentrations. Incubation of human NIP cells with GLP-1 or exendin-4 induced insulin expression in subsets of cells, and also produced changes in cellular morphology. GLP-1R agonists also induced insulin secretion in ~30% of NIP clones. Intriguingly, NIP cultures that approached confluence expressed the proglucagon gene and secreted GLP-1 into the culture medium, raising the possibility of an autocrine GLP-1-differentiation loop in these cells. See Abraham et al., Endocrinology 143(8): 3152-61, 2002.

Exendin-4 has also been shown to enhance Pdx-1 expression, but not insulin expression, in human islet-like cell clusters treated for 4 days in vitro, and exendin-4 treatment of rats (10 days of injections initiated 48 hrs after the transplantation procedure) with transplanted clusters induced functional maturation of transplanted cells, and promoted the differentiation and growth of clusters transplanted under the kidney capsule, as assessed 8 weeks following the transplant. See Movassat et al., J. Clin. Endocrinol. Metab. 87(10): 4775-4781, 2002.

Several lines of evidence support a role for GLP-1 in the control of islet proliferation and regeneration in rodent studies in vivo. Administration of subcutaneous GLP-1 for 2 days to lean mice increased the islet labeling index, as shown by Edvell and Lindstrom in Endocrinology 140(2): 778-83, 1999. Initiation of increased pancreatic islet growth in young normoglycemic mice (Umea +/?). In complementary studies using normal rats and the rat pancreatectomy model, Xu et al demonstrated that exendin-4 increases islet neogenesis and β cell proliferation. Furthermore, exendin-4 attenuates glucose intolerance following partial pancreatectomy in the rat. Diabetes 48(12): 2270-6, 1999. Exendin-4 stimulates both beta-cell replication and neogenesis, resulting in increased beta-cell mass and improved glucose tolerance in diabetic rats. Similarly, infusion of GLP-1 for 5 days in both young and old rats increased β cell mass and promoted enhanced pdx-1 expression and islet neogenesis Glucagon-like peptide-1 induces cell proliferation and pancreatic-duodenum homeobox-1 expression and increases endocrine cell mass in the pancreas of old, glucose-intolerant rats. Perfetti et al., Endocrinology 141(12): 4600-5, 2000.

If administered to young 6 week old prediabetic db/db mice, daily exendin-4 treatment for 2 weeks prevented the progression to more severe diabetes, in association with expansion of islet mass and improved glucose tolerance and insulin secretion. See Wang and Brubaker Diabetologia 45(9): 1263-73, 2002. Similarly, NN2211 and exendin-4 increased β cell proliferation in db/db mice, but not in ob/ob mice, as shown in Rolin et al., Am. J. Physiol. Endocrinol. Metab. 283(4): E745-52, 2002 and islet proliferative effects were also detected following a 2 week treatment period with exendin-4 in young db/db mice. See Wang and Brubaker, Diabetologia. 45(9): 1263-73, 2002.

Administration of the GLP-1R agonist Liraglutide (NN2211) to normal and ZDF rats as well as to 60% pancreatectomized rats demonstrated that the ability of Liraglutide to expand b cell mass was correlated with the metabolic milieu, and the duration of treatment, with normoglycemic normal animals failing to show an increase in b cell mass, whereas hyperglycemic animals responded to Liraglutide with an increase in b cell mass. Similarly, b cell mass was increased in non-diabetic Sprague-Dawley rats treated with Liraglutide for 1 week, but after 6 weeks of treatment, b cell mass was comparable in treated vs control rats, as described in The endocrine pancreas in non-diabetic rats after short-term and long-term treatment with the long-acting GLP-1 derivative NN2211. Bock et al., APMIS. 111 (12): 1117-1124, 2003. Hence, the trophic effects of GLP-1R agonists in the islet, like their insulinotropic properties, are probably coupled to the presence of hyperglycemia. See Sturis et al., Br J. Pharmacol. 140(1): 123-132, 2003.

Complementary studies of GLP-1 or exendin-4 administration for 5 days in the neonatal GK rat demonstrate persistent improvement in glucose homeostasis, enhanced pancreatic insulin content and total beta-cell mass due to stimulation of beta-cell neogenesis and regeneration. Follow-up from day 7 to adult age (2 months) demonstrated GLP-1 or Ex-4 treated rats maintained enhanced beta-cell mass and improved glycemic control at adult (2 months) age. See Tourrel et al., Diabetes. 51(5): 1443-1452, 2002.

The finding of only modest and subtle abnormalities in islet development in GLP-1R−/− mice suggest that islets develop normally in the absence of GLP-1R signaling. Furthermore, the development of islet hyperplasia and hyperinsulinemia in the setting of insulin resistance, hyperglycemia and leptin deficiency is not compromised in the ob/ob:GLP-1R−/− mutant mouse. Hence it appears that although activation of GLP-1R signaling stimulates islet neogenesis and proliferation, the GLP-1R signaling pathway is not required for islet adaptation in the mouse in vivo. See Scrocchi et al., Diabetes 49(9): 1552-60, 2000.

A complementary approach to address the importance of endogenous GLP-1 receptor expression for b cell regeneration involves analysis of the islet regenerative responsive to partial pancreatectomy. Wildtype mice subjected to partial pancreatectomy were infused with the antagonist exendin(9-39); partial pancreatectomy was also carried out in GLP-1R−/− mice. In Ex(9-39)-treated sham-operated mice, persistent fasting hyperglycemia was observed, but b cell mass was not diminished. In pancreatectomized mice, persistent glucose intolerance was noted, but this was not further exacerbated by Ex(9-39) and recovery of b cell mass in Ppx mice was not impaired. In contrast, GLP-1R(−/−) mice exhibited greater hyperglycemia after pancreatectomy compared with wild-type mice, and this correlated with a significant defect in regeneration of b cell mass. Hence, the importance of endogenous GLP-1R signaling following partial pancreatectomy depends on the experimental context. See Role of Endogenous Glucagon-Like Peptide-1 in Islet Regeneration After Partial Pancreatectomy. De Leon et al., Diabetes 52(2): 365-371, 2003.

These new findings add yet another important mechanism to the broad spectrum of GLP-1 actions which converge on lowering blood glucose in vivo. Furthermore, the possibility that activation of GLP-1 signaling might be therapeutically useful for regeneration of β cell mass has important implications for the treatment of Type 1 and Type 2 Diabetes.

Several studies address the possibility that islet A cell may produce GLP-1 in the context of islet development or regeneration, by demonstrating induction of PC1 expression in A cells, the prohormone convertase responsible for liberating GLP-1 from proglucagon. Pancreatic and A cell expression of PC1 is induced in rats given streptozotocin, leading to small but significant increases in the levels of bioactive GLP-1 in the rat pancreas Regulation of pancreatic PC1 and PC2 associated with increased glucagon-like peptide 1 in diabetic rats. Nie et al., J. Clin. Invest. 105(7): 955-65, 2000. A second study documents the developmental expression of proglucagon and PC1 in the embryonic mouse pancreas from E10.5 to E 15.5 Expression pattern of IAPP and prohormone convertase ⅓ reveals a distinctive set of endocrine cells in the embryonic pancreas. Wilson et al., Mech. Dev. 115(1-2): 171-176, 2002, raising the possibility that bioactive GLP-1 might be liberated from these cells with potential implications for β cell growth and development. These studies do not prove that bioactive GLP-1 exerts a role during development or regeneration, but they certainly expand our concepts to include a potential for some islet A cells to produce GLP-1 in the correct developmental or experimental setting.

GLP-1 in CNS

There is also considerable study in the role(s) of GLP-1 in CNS in the control of satiety and food intake. A large body of evidence demonstrates that ICV GLP-1 can reduce food intake in both acute and chronic studies. Conversely, ICV administration of the GLP-1 antagonist exendin (9-39) can acutely increase food intake and promote weight gain in chronic rodent studies. These satiety-related effects have also been observed in human studies with peripheral administration of GLP-1 to both normal and diabetic subjects.

CNS GLP-1 is synthesized largely in the brainstem and transported along axonal networks to diverse CNS regions, including the hypothalamus. The GLP-1 receptor has been localized to numerous CNS nuclei using a combination of receptor autoradiography or in situ hybridization studies. The studies by Turton, Bloom and colleagues demonstrated that ICV GLP-1 clearly inhibits food intake (Nature 379(6560): 69-72, 1996).

Peripheral administration of GLP-1 is taken up into the CNS, as illustrated by Kastin et a. in J. Mol. Neurosci. 18(1-2): 7-14, 2002. Administration of the radio-labeled protease-resistant analogue [Ser8]GLP-1, revealed uptake of this peptide into the CNS that was not saturable, nor competed by wildtype GLP-1 or the GLP-1 receptor antagonist exendin(9-39), suggesting that the GLP-1 receptor is not involved in the rapid entry into brain. [Ser8]GLP-1 was detected within the brain parenchyma, but a large proportion was loosely associated with the vasculature at the BBB. These studies demonstrate that a radio-labeled GLP-1 analogue can enter the brain. Similar studies using CD1 mice have demonstrated that exendin-4 readily crosses the blood brain barrier, even more efficiently than native GLP-1, as illustrated by Kastin and Akerstrom in Int. J. Obes. Relat. Metab. Disord. 27(3): 313-318, 2003.

GLP-1 is also implicated in aversive stimulation and stress in CNS. Although the data linking GLP-1 to inhibition of food intake are quite solid, it is also important to consider a role for GLP-1 in the CNS response to aversive stimuli. A link between GLP-1 and the stress response was first suggested, albeit indirectly, by studies from Larsen and colleagues who demonstrated that ICV GLP-1 activated hypothalamic CRH+ neuroendocrine neurons leading to increased corticosterone secretion in rats Central administration of glucagon-like peptide-1 activates hypothalamic neuroendocrine neurons in the rat. Larsen et al., Endocrinology 138(10): 4445-55, 1997.

More recent experiments have confirmed the intricate anatomical association between GLP-1R+ nerve terminals in neuronal projections that abut CRH+ neurons in the hypothalamic PVN, as described in Sarkar et al., Brain Res. 985(2): 163-8, 2003.

A series of experiments also demonstrated that many of the aversive effects of Lithium chloride administration in rats are blocked by ICV preadministration of exendin (9-39), the GLP-1 receptor antagonist, as illustrated in Seeley et al., J. Neurosci. 20(4): 1616-21, 2000.

To localize the CNS regions responsive to GLP-1 that mediate the anorexic versus visceral illness (CTA) effects of GLP-1, Kinzig and colleagues injected various doses of GLP-1 into the lateral or 4th ventricle of rats. Both sites could transduce a GLP-1 signal linked to food intake, whereas only GLP-1 instilled into the lateral ventricle evoked a CTA response. The central nucleus of the amygdala was identified as a key GLP-1R+ site important for the response to visceral illness. These findings illustrate the compartmentalization of the CNS GLP-1R response to differential CNS inputs as outlined in Kinzig et al., J. Neurosci. 22(23): 10470-6, 2002. Similar experiments demonstrated that the endocrine component of the stress response is activated following GLP-1 injection into the hypothalamic PVN, whereas the anxiety response is induced by GLP-1 administration in the central nucleus of the amygdala. See Kinzig et al., J. Neurosci. 23(15): 6163-70, 2003.

Other studies corroborate the GLP-1-mediated activation of stress-related signaling pathways in the CNS. The data in Interoceptive stress activates glucagon-like peptide-1 neurons that project to the hypothalamus. Rinaman (Am. J. Physiol. 277(2 Pt 2): R582-590, 1999) demonstrates that LiCl, LPS and CCK activate GLP-1 neurons, whereas the same neurons are not activated following ingestion of a large meal. A similar story emerges in "A functional role for central glucagon-like peptide-1 receptors in lithium chloride-induced anorexia," by Rinaman, Am. J. Physiol. 277(5 Pt 2): R1537-40, 1999. Central infusion of the GLP-1 antagonist exendin (9-39) increases the febrile response to LPS, suggesting that GLP-1R signaling may normally function to attenuate the response in vivo. See Rinaman and Corner, Auton. Neurosci. 85(1-3): 98-101, 2000.

Complementary studies in mice demonstrate that several behavioral tests that reflect anxiety, as well as the corticosterone response to stress, are abnormal in the absence of intact GLP-1R signaling. See MacLusky et al., Endocrinology 141 (2):752-62, 2000.

GLP-1 is also found to have central and peripheral cardiovascular effects.

Blazquez et al. have demonstrated that both i.v and peripheral GLP-1 administration increase heart rate and blood pressure in rats. See Barragan et al., Am. J. Physiol. 266(3 Pt 1): E459-66, 1994; Barragan et al., Regul. Pept. 67(1): 63-8, 1996; Barragan et al., Am. J. Physiol. 277(5 Pt 1): E784-91, 1999. Similar observations have been made by Edwards et al., Exp. Physiol. 82(4): 709-16, 1997. The hypertensive and chronotropic actions of GLP-1 in the rat are evident even in the setting of hypovolemia, and associated with further augmentation of circulating vasopressin and oxytocin, as shown by Bojanowska and Stempniak in J. Endocrinol. 172(2): 303-310, 2002.

More recent studies have demonstrated that even moderate doses of GLP-1 agonists at levels not sufficient to lower blood glucose result in activation of central sympathetic neurons and adrenal medullary chromaffin cells that produce catecholamines. Centrally and peripherally administered GLP-1R agonists including native GLP-1 and the lizard peptide exendin-4 dose-dependently increased blood pressure and heart rate in rats. GLP-1R activation induced c-fos expression in the adrenal medulla and neurons in autonomic control sites in the rat brain, including medullary catecholamine neurons providing input to sympathetic preganglionic neurons. Furthermore, GLP-1R agonists rapidly activated tyrosine hydroxylase transcription in AP neurons which express the GLP-1R, as shown in Yamamoto et al., J. Neurosci. 23(7): 2939-2946, 2003. These findings suggest that the central GLP-1 system represents a regulator of sympathetic outflow leading to downstream activation of cardiovascular responses in the rodent, and are consistent with previous reports demonstrating that GLP-1R systems function as a component of neural networks transducing the CNS response to aversive stimuli. See Yamamoto et al., J. Clin. Invest. 110: 43-52, 2002.

ICV GLP-1 has also been shown to increase fecal output in rats, and these actions were blocked by treatment with either exendin (9-39) or the CRF receptor antagonist, astressin. Hence, these findings provide yet another link between GLP-1 actions in the CNS, stress, and the CRH pathway. See Ali Gülpinar et al., AJP—Gastrointest. Liver. Physiol. 278: G924-G929, 2000.

There might also be a connection between leptin and GLP-1 in the CNS. It was suggested that GLP-1 may be downstream of leptin action in the brain. Indeed, some studies show that leptin activates a subset of GLP-1 neurons in the brainstem. Elias et al., J. Comp. Neurol. 423(2): 261-81, 2000. Nevertheless, GLP-1 receptor signaling is not required for leptin action in the CNS. Scrocchi et al., Diabetes 49: 1552-1560, 2000.

GLP-1 may also has neuroprotection, learning and memory function in the CNS. A study in rats infused with an exendin (5-39) GLP-1R antagonist demonstrated decreased neurotoxicity following infusion with beta amyloid protein. See Oka et al., Brain Res. 878(1-2): 194-198, 2000. In contrast, studies using the rat PC12 pheochromocytoma cell line, which expresses the GLP-1 receptor, suggest that GLP-1 agonists promote neurite outgrowth and NGF-induced differentiation, and may enhance cell survival following withdrawal of NGF, depending on the timing of exendin-4 administration. The differentiation actions of GLP-1 were abrogated by the kinase inhibitors LY294002 or PD98059, but the PKA inhibitor H-89 had only modest effects on these actions. Hence, these findings suggest that GLP-1R signaling, perhaps independent of PKA activation, may be neurotrophic in the correct cellular context. See Perry et al., J. Pharmacol. Exp. Ther. 300(3): 958-66, 2002. Another study demonstrated that GLP-1, and exendin-4, can completely protect cultured rat hippocampal neurons against glutamate-induced apoptosis, and both GLP-1 and exendin-4 reduced ibotenic acid-induced depletion of choline acetyltransferase immunoreactivity in rat basal forebrain cholinergic neurons. Similarly, GLP-1 can reduce the levels of amyloid-beta peptide (Abeta) in the brain in vivo and reduced levels of amyloid precursor protein (APP) in cultured neuronal cells. Furthermore, GLP-1 and exendin-4 protect cultured hippocampal neurons against death induced by Abeta and iron See Perry et al., J. Neurosci. Res. 72(5): 603-12, 2003.

Hence, these results suggests that GLP-1 action in the brain may be neuroprotective, perhaps via activation of anti-apoptotic signaling pathways in specific neurons. See Perry et al., J. Pharmacol. Exp. Ther. 302(3): 881-8, 2002.

During et al. have shown, using a variety of gene therapy, and peptide-based technologies, that activation of CNS GLP-1R signaling enhances associative and spatial learning through GLP-1R. These investigators used a novel N-terminal exendin-4 derivative, [Ser(2)]exendin(1-9), which when administered peripherally, gains access to the CNS, and activates the CNS GLP-1R system. GLP-1R-deficient mice exhibit a learning deficit phenotype which is restored after hippocampal GLP-1R gene transfer. Furthermore, gain of function studies in rats overexpressing the GLP-1R in the hippocampus show improved learning and memory. GLP-1R-deficient mice also have enhanced seizure severity and neuronal injury after kainate administration, with correction after GLP-1R gene transfer in hippocampal somatic cells. Systemic administration of the GLP-1R agonist peptide [Ser(2)]exendin(1-9) in wild-type animals prevents kainate-induced apoptosis of hippocampal neurons. See During et al., Nat. Med. 9(9): 1173-9, 2003 (Epub 2003 August 17).

GLP-1 and Food Intake

Following the publication of data demonstrating that ICV GLP-1 dose-dependently inhibits food intake (Wilding et al., Nature 379(6560): 69-72, 1996), subsequent studies demonstrated that blockade of CNS GLP-1 action using ICV infusion of exendin (9-39) increased food intake and promoted weight gain in rats. Meeran et al., Endocrinology 140(1): 244-50, 1999. Similarly, injection of exendin (9-39) into the lateral hypothalamus increased food intake in satiated rats. Schick et al., Am. J. Physiol. Regul. Integr. Comp. Physiol. 284(6): R1427-35, 2003.

Over the last several years, the evidence linking GLP-1 action in the CNS to regulation of food intake and body weight has been confirmed by multiple independent laboratories. Although the PVN of the hypothalamus was the initial focus of studies linking GLP-1 actions to satiety, several studies have now demonstrated, using direct injection approaches, that multiple brain regions are capable of transducing a CNS satiety effect in response to GLP-1, including the LH, DMH, and VMH, as shown in Kinzig et al., J. Neurosci. 22(23): 10470-6, 2002; Schick et al., Am. J. Physiol. Regul. Integr. Comp. Physiol. 284(6): R1427-35, 2003.

Furthermore, it is clear that peripheral administration of long-acting GLP-1 agonists to diabetic rodents can also reduce food intake and achieve weight loss, in studies of several weeks duration. The Novo Nordisk GLP-1 analogue NN2211 induced weight loss in both lean control rats and in MSG-lesioned rats, hence the anorectic actions were presumably mediated by signaling systems outside the region of the hypothalamus affected by neonatal monosodium glutamate administration. To review the experimental data, including analyses of body composition after NN2211, see Larsen et al., Diabetes 50 (11): 2530-2539, 2001.

Over a dozen human studies in both normal subjects and in patients with obesity or type 2 diabetes have examined the relationship between GLP-1 infusion and food intake. The majority of studies have shown a small but significant inhibition of short-term food intake with concurrent GLP-1 infusion. A Meta-Analysis of these studies has concluded that there is a dose-dependent reduction in food intake associated with a reduction of gastric emptying in human subjects. See Verdich et al., J. Clin. Endocrinol. Metab. 86(9): 4382-9, 2001.

An important but as yet not-so-well-understood phenomenon surrounds the effects of intermittent vs. continuous GLP-1 administration on food intake and body weight. GLP-1 given by subcutaneous injection 30 minutes before meals in a 5 day randomized cross-over study of obese human subjects was more effective in producing weight loss relative to a continuous 5 day subcutaneous GLP-1 infusion. However, a key difference between the different arms of the study was the peak plasma level of GLP-1 achieved, which was significantly higher (269.4 vs. 88.7 pM) in the patients given subcutaneous injections. Hence, it is not possible to make firm conclusions as to whether peripheral vs. continuous GLP-1 delivery exerts differential effects on weight loss. See Naslund et al., Br. J. Nutr. 91(3): 439-46, 2004.

GLP-1 and Gastric Emptying

Although GLP-1 was originally identified as a β cell secretagogue, a considerable body of experimental evidence in rodents, pigs and human studies demonstrates that GLP-1 is a potent regulator of gastrointestinal motility and gastric secretion. This action of GLP-1 accounts for the observation that glycemic excursion is often blunted and insulin secretion is frequently attenuated, following oral nutrient ingestion in the setting of co-administered exogenous GLP-1. These properties of GLP-1, taken together with the tight correlation between the levels of circulating GLP-1 and the rate of gastric emptying (Wishart et al., Peptides 19(6): 1049-53, 1998), have prompted some to opine that the gastric emptying actions of GLP-1 may be as or more important than the "incretin" actions of GLP-1, as outlined in Nauck et al., Am. J. Physiol. 73(5 Pt 1): E981-8, 1997; Nauck Diabetologia 42(3): 373-9, 1999.

Indeed, the potent dose-dependent inhibition of gastric emptying observed following GLP-1 infusion in human subjects with Type 2 diabetes will produce significant lowering of meal-related glycemic excursion, even without any increase in levels of circulating insulin, as outlined in Meier et al., J. Clin. Endocrinol. Metab. 88(6): 2719-25, 2003.

A direct role for GLP-1 in gastric physiology was shown by demonstrating stimulation of cAMP formation in rat gastric gland preparations and the human HGT-1 human cancer cell line. See Hansen et al., FEBS Lett. 236(1): 119-22, 1988, which was followed by the demonstration that GLP-1 also inhibited pentagastrin-stimulated gastric acid secretion in human studies at physiologically relevant concentrations. See Schjoldager et al., Dig. Dis. Sci. 34(5): 703-8, 1989; O'Halloran et al., J. Endocrinol. 126(1): 169-73, 1990. C.f. Nauck et al., Digestion 52(3-4): 214-21, 1992. However, the effect of GLP-1 on inhibition of gastric acid secretion is lost in human subjects previously subjected to a vagotomy for control of ulcer disease. See Wettergren et al., Gut. 40(5): 597-601, 1997. Similarly, the vagal afferents play an important role in mediating both the central and peripheral effects of GLP-1 on gastric emptying in rats, as shown in Imeryuz et al., Am. J. Physiol. 273(4 Pt 1): G920-7, 1997. Rat studies have also shown potent inhibition of small bowel motility. Tolessa et al., Dig. Dis. Sci. 43(10): 2284-90, 1998. Vagal innervation is also important for the inhibitory effects of GLP-1 on gut motility in pigs. Wettergren et al., Am. J. Physiol. 275(5 Pt 1): G984-92, 1998. Pharmacological levels of GLP-1 appear to inhibit both gastric emptying and gastric acid secretion in normal human subjects (Wettergren et al., Dig. Dis. Sci. 38(4): 665-73, 1993) and in obese subjects (Naslund et al., Am. J. Clin. Nutr. 68(3): 525-30, 1998). In addition, administration of exendin (9-39) to gastric fistula rats reverses the glucose meal-induced inhibition of gastric emptying if the antagonist is given peripherally, but not following icv injection. See Schepp et al., Am. J. Physiol. 273(4 Pt 1): G920-7, 1997.

In studies using rat parietal cell preparations, both exendin-4 and GLP-1 display similar properties with respect to H+ and cAMP production and the actions of these peptides are blocked by the GLP-1 receptor antagonist exendin(9-39). Schepp et al., Eur. J. Pharmacol. 269(2): 183-91, 1994.

The inhibitory effect of GLP-1 on gastric emptying likely accounts for at least part of the glucose-lowering effects observed in Type 1 diabetic patients (Dupre et al., Diabetes 44(6): 626-30, 1995). GLP-1 also inhibits gastric emptying in subjects with type 2 diabetes following a liquid test meal (Willms et al., J. Clin. Endocrinol. Metab. 81(1): 327-32, 1996; Diabetologia 39(12): 1546-53, 1996), and following ingestion of only water (Naslund et al., Scand. J. Gastroenterol. 36(2): 156-62, 2001), or following ingestion of a solid meal (Naslund et al., Am. J. Physiol. 277(3 Pt 2): R910-6, 1999; Delgado-Aros et al., Am. J. Physiol. Gastrointest. Liver. Physiol. 282(3): G424-31, 2002). The inhibitory effects of GLP-1 on GI motility are also detected in human studies in the inter-digestive state (Schirra et al., Gut 46(5): 622-31, 2000; Shirra et al., Gut 50(3): 341-8, 2002).

The glucose-lowering effect of the drug acarbose may be attributed in part to the inhibition of gastric emptying perhaps due to the increase in levels of circulating GLP-1 that are detected following acarbose administration (Ranganath et al., Diabet. Med. 15(2): 120-4, 1998; Enc et al., Am. J. Physiol. Gastrointest. Liver. Physiol. 281(3): G752-63, 2001). Co-administration of acarbose and sucrose leads to a delay and sustained release of GLP-1 in human subjects (Seifarth et al., Diabet. Med. 15(6): 485-91, 1998).

GLP-1 and the Cardiovescular System

In February 2004, a pilot study reported the effect of acute GLP-1 administration in 10 human subjects with LV dysfunction and acute MI following angioplasty. Native GLP-1 was administered as a 72-hour infusion at a rate of 1.5 pmol/kg per minute. Echocardiograms were obtained after reperfusion and after the completion of the GLP-1 infusion. GLP-1 significantly improved LVEF (from 29+2% to 39+2%, P<0.01), global wall motion score indexes (1.94+0.11 to 1.63+0.09, P<0.01), and regional wall motion score indexes (2.53+0.08 to 2.02+0.11, P<0.01) compared with control subjects. The benefits of GLP-1 were independent of AMI location or history of diabetes. GLP-1 administration was accompanied by a significant decrease in plasma glucose and free fatty acids and was associated with reduced mortality and duration of hospital stay. See Nikolaidis et al., Circulation 109(8): 962-5, 2004 (Epub 2004 Feb. 23).

GLP-1 administered intravenously or by ICV injection increases heart rate and blood pressure in rats. See Barragan et al., Am. J. Physiol. 266(3 Pt 1): E459-66, 1994; J. Biol. Chem. 275(44): 34471-7, 2000. These effects can be blocked by intravenous or ICV administration of the antagonist exendin(9-39) and bilateral vagotomy blocked the cardiovascular effects of ICV, but not peripherally administered GLP-1 (Barragan et al., Am. J. Physiol. 277(5 Pt 1): E784-91, 1999). Analysis of direct GLP-1 actions on cardiac muscle cells was studied using cultures of rat cardiac myocytes. Although GLP-1 increased intracellular cAMP in cardiac myocytes, in contrast to the positive inotropic actions of isoproterenol, GLP-1 induced a decrease in contraction amplitude with no change in intracellular calcium transit. Furthermore, both isoproterenol and GLP-1 produced an intracellular acidosis. Hence, these findings demonstrate that coupling of cardiomyocyte GLP-1R signaling to cAMP generation produces distinct downstream signaling events when compared to adrenergic agonists. See Vila et al., Circ. Res. 89(5): 445-452, 2001.

Even moderate doses of GLP-1 agonists infused at levels not sufficient to lower blood glucose result in activation of central sympathetic neurons and adrenal medullary chromaffin cells that produce catecholamines. Centrally and peripherally administered GLP-1R agonists including native GLP-1 and the lizard peptide exendin-4 dose-dependently increased blood pressure and heart rate in rats. GLP-1R activation induced c-fos expression in the adrenal medulla and neurons in autonomic control sites in the rat brain, including medullary catecholamine neurons providing input to sympathetic preganglionic neurons. Furthermore, GLP-1R agonists rapidly activated tyrosine hydroxylase transcription in AP neurons which express the GLP-1R, as shown in Yamamoto et al., J. Neurosci. 23(7): 2939-2946, 2003.

These findings suggest that the central GLP-1 system represents a regulator of sympathetic outflow leading to downstream activation of cardiovascular responses in the rodent, and are consistent with previous reports demonstrating that GLP-1R systems function as a component of neural networks transducing the CNS response to aversive stimuli. See Yamamoto et al., J. Clin. Invest. 110: 43-52, 2002.

The importance of cholinergic and nicotinic acid receptors for transduction of the central cardiovascular response to GLP-1 was determined in normal rats. The nicotinic receptor antagonist mecamylamine and the muscarinic receptor antagonist atropine prevented the stimulatory effect of GLP-1 on blood pressure whereas only mecamylamine blocked the GLP-1-dependent increase in heart rate. Intraarterial application of a V(1) receptor antagonist blocked the GLP-1 effects on blood pressure. See Isbil-Buyukcoskun and Gulec, Regul Pept. 118(1-2): 33-8, 2004.

In contrast to data suggesting that acute administration of GLP-1 may increase heart rate and blood pressure in rodents, chronic 14 day treatment of salt-sensitive rats on a high salt diet with recombinant GLP-1 reduced the development of hypertension, proteinuria and improved endothelial function with decreased renal and cardiac damage. The authors postulated that the protective effects of GLP-1 were attributable to increased urine flow and sodium excretion notable for the first 3 days following elevation in sodium intake. See Yu et al., J. Hypertens. 21(6): 1125-1135, 2003.

GLP-1 Treatment in Human Subjects

To date, almost all of the actions reported for GLP-1 in animal studies have been validated in several dozen human studies of both normal and diabetic subjects. The glucose-lowering actions of GLP-1 in studies of diabetic patients are secondary to inhibition of gastric emptying and glucagon secretion, and stimulation of insulin secretion. GLP-1 also lowers appetite in short term studies of patients with type 2 diabetes, however the long terms effects of GLP-1 or exendin-4 on body weight in diabetic subjects have not yet been reported.

Enhanced interest in the potential use of GLP-1 for the treatment of diabetes followed the NEJM publication demonstrating that GLP-1 lowered blood glucose in both patients with Type 2 and Type 1 diabetes (Gutniak et al., N. Engl. J. Med. 326(20): 1316-22, 1992).

Although the majority of interest in GLP-1 as a therapeutic agent is focused on Type 2 diabetes, several studies have shown modest glucose-lowering effects of GLP-1 administration in Type 1 diabetes, likely due to effects on gastric emptying and inhibition of glucagon secretion. See Vella et al., Diabetes 50(3): 565-72, 2001; Creutzfeldt et al., Diabetes. Care 19(6): 580-6, 1996; Dupre et al., Diabetes 44(6): 626-30, 1995.

Although there has been some controversy about whether GLP-1 stimulates insulin-independent glucose uptake, some studies have suggested GLP-1 promotes insulin or glucagon-independent glucose clearance and/or suppression of glucose production. Studies of endogenous glucose production (Ra) and glucose disposal (Rd) in 8 human volunteers were carried out with fixed insulin and glucagon concentrations (octreotide infusion) while glucose was maintained at the fasting level and insulin and glucagon were replaced to maintain blood glucose near fasting levels. A 60 minute infusion of GLP-1 (30 pmol/kg/h) decreased plasma glucose in all 8 subjects which was accounted for by a significant, 17% decrease in Ra, with no significant change in Rd. Hence, GLP-1 may lower fasting blood glucose in normal individuals through effects on the liver, possibly through portal neural mechanisms. See Prigeon et al., Am. J. Physiol. Endocrinol. Metab. 285(4): E701-7, 2003 (Epub 2003 May 28).

GLP-1 functions as an incretin in human subjects, as infusion of the GLP-1 antagonist exendin (9-39) blocked the insulinotropic and glucagonostatic effects of exogenous GLP-1, and also increased plasma glucagon during euglycemia and hyperglycemia. Exendin (9-39 also increased insulin during hyperglycemia. These findings agree with similar studies in rodent "loss of function" models, and demonstrate the physiological importance of GLP-1 action for glucose regulation in normal human subjects. See Schilla et al., J. Clin. Invest. 101(7): 1421-30, 1998. Similarly, blockade of endogenous GLP-1 with Glucagon-like peptide 1 has a physiological role in the control of postprandial glucose in humans (Edwards et al., Diabetes 48(1): 86-93, 1999).

Other Biological Effects of GLP-1

As described above, although the principal focus of GLP-1 research has been on pleiotropic actions that ultimately converge on regulation of nutrient intake and disposal through effects on CNS satiety centers, gastrointestinal motility, islet function and β cell growth, the GLP-1 receptor is widely expressed in several tissues not considered classic metabolic regulators of energy homeostasis, such as the heart, kidney, and lungs.

GLP-1 and hypothalamic-pituitary function: Although much recent attention has focused on the role of hypothalamic GLP-1 in the control of food intake, GLP-1 may also regulate the hypothalamic pituitary axis (HPA) via effects on LH, TSH, CRH, oxytocin and vasopressin secretion. See Beak et al., Endocrinology 137(10): 4130-8, 1996; Beak et al., J. Clin. Invest. 101(6): 1334-41, 1998; Larsen et al., Endocrinology 138(10): 4445-55, 1997. But these GLP-1 actions do not appear to be essential for HPA function, as GLP-1R−/− mice cycle normally, are fertile, and exhibit normal basal levels of plasma osmolarity, corticosterone, thyroid hormones, estradiol, and testosterone (MacLusky et al., Endocrinology 141 (2): 752-62, 2000.

GLP-1 and the lung: GLP-1 receptor mRNA transcripts have been localized to the lung in rodents and humans, and several studies have confirmed the presence of GLP-1 binding sites using rat lung membrane preparations. Several reports have suggested that GLP-1 may exert actions both on airways (tracheal rings) and on pulmonary vasculature. Addition of GLP-1 to lung preparations increased macromolecule secretion and relaxed preconstricted pulmonary arteries. See Richter et al., Am. J. Physiol. 265(4Pt1): L374-81, 1993. Subsequent studies demonstrated that GLP-1 increases pulmonary surfactant production from isolated rat pneumocytes (Vara et al., Endocrinology 139(5): 2363-8, 1998) and similar studies have also been carried out using human lung cells (Vara et al., Am. J. Respir. Crit. Care. Med. 163(4): 840-846, 2001.

GLP-1 action in fat and muscle cells: GLP-1 has been shown to exert modest effects on fat and muscle cells in vitro. Nevertheless, there continue to be reports describing actions of GLP-1 on muscle, including studies with human muscle cells and strips, suggesting actions of glucagon-like peptide agonists and antagonists. In muscle strips, GLP-1 stimulated glycogen synthesis, glycogen synthase a activity, and glucose oxidation and utilization, and inhibited glycogen phosphorylase a activity. In cultured myotubes, GLP-1 at very low doses of 0.1-1 pM stimulated glucose incorporation into glycogen. Curiously, exendin-4 and its truncated form 9-39 amide (Ex-9) both exert the same types of effects on glycogen synthesis and synthase a activity without stimulating an increase in cAMP accumulation. See Luque et al., J. Endocrinol. 173(3): 465-73, 2002.

Equivalents

Those skilled in the art will know or be able to ascertain using no more than routine experimentation, many equivalents to the embodiments and practices described herein. Accordingly, it will be understood that the invention is not to be limited to the embodiments disclosed herein.

The contents of all references, patents and published patent applications cited throughout this application, as well as the Figures are hereby incorporated by reference.

The invention claimed is:

1. A device for delivering an effective amount of a GLP-1 compound to a patient in need of GLP-1 receptor stimulation comprising:
   (a) a fluid storage chamber containing a GLP-1 compound, said fluid storage chamber having an output orifice through which said GLP-1 compound can be expelled;
   (b) a pump chamber functionally connected to said fluid storage chamber by a moveable barrier, wherein the rate of movement of said moveable barrier caused by said pump chamber is adjustable to produce variable dosing under patient control;
   (c) a hydraulic fluid reservoir functionally connected to a first actuator and having a high viscosity fluid stored therein, said hydraulic fluid reservoir fluidly connected to said pump chamber by a fixed aperture; and
   (d) a second actuator which physically acts on said pump chamber, wherein said second actuator is controlled independently of said first actuator;
   wherein said pump chamber continuously expands upon actuation of said device with said first actuator;
   wherein operating said first actuator causes said high viscosity fluid to flow into said pump chamber through said fixed aperture at a constant rate, thereby displacing said moveable barrier to compress said fluid storage chamber and causing a quantity of said GLP-1 compound to be expelled through said orifice;
   wherein operating said second actuator independently causes displacement of said moveable barrier to compress said fluid storage chamber, thereby causing a quantity of said GLP-1 compound to be expelled; and
   wherein concurrently operating both of said first and second actuators causes displacement of the moveable barrier to compress said fluid storage chamber at an increased rate relative to operating either actuator alone.

2. The device of claim 1, wherein said GLP-1 compound is GLP-1.

3. The device of claim 1, wherein said GLP-1 compound is a GLP-1 analog with substantially the same or better potency than that of GLP-1.

4. The device of claim 1, wherein said GLP-1 compound is a derivative of GLP-1 or GLP-1 analog, each of which has substantially the same or better potency than that of GLP-1.

5. The device of claim 1, further comprising a needle functionally connected to the output orifice for delivery of GLP-1 compound expelled from said fluid storage chamber to an individual.

6. The device of claim 1, wherein said first actuator comprises two or more springs.

7. The device of claim 1, wherein said second actuator comprises two or more springs.

8. The device of claim 1, wherein the viscosity of said high viscosity fluid is about ISO VG 1500 or more.

9. The device of claim 1, wherein said first actuator causes constant delivery of said GLP-1 compound, and said second actuator causes a bolus delivery of said GLP-1 compound under patient control.

10. The device of claim 1, wherein said first actuator generates a force of from about 0.001 lbs to about 10 lbs.

11. A method of stimulating a GLP-1 receptor in a subject in need of such stimulation, said method comprising the step of administering to a patient an effective amount of a GLP-1 compound using a device comprising:
   (a) a fluid storage chamber containing a GLP-1 compound, said fluid storage chamber having an output orifice through which said GLP-1 can be expelled;
   (b) a pump chamber functionally connected to said fluid storage chamber by a moveable barrier, wherein the rate of movement of said moveable barrier caused by said pump chamber is adjustable to produce variable dosing under patient control;
   (c) a hydraulic fluid reservoir functionally connected to a first actuator and having a high viscosity fluid stored therein, said hydraulic fluid reservoir fluidly connected to said pump chamber by a fixed aperture; and
   (d) a second actuator which physically acts on said pump chamber, wherein said second actuator is controlled independently of said first actuator;
   wherein said pump chamber continuously expands upon actuation of said device with said first actuator;
   wherein operating said first actuator causes said high viscosity fluid to flow into said pump chamber through said fixed aperture at a constant rate, thereby displacing said moveable barrier to compress said fluid storage chamber and causing a quantity of said GLP-1 compound to be expelled through said orifice;
   wherein operating said second actuator independently causes displacement of said moveable barrier to compress said fluid storage chamber, thereby causing a quantity of said GLP-1 compound to be expelled; and
   wherein concurrently operating both of said first and second actuators causes displacement of the moveable barrier to compress said fluid storage chamber at an increased rate relative to operating either actuator alone.

12. The method of claim 11, wherein said GLP-1 compound is GLP-1.

13. The method of claim 11, wherein said GLP-1 compound is a GLP-1 analog with substantially the same or better potency than that of GLP-1.

14. The method of claim 11, wherein said GLP-1 compound is a derivative of GLP-1 or GLP-1 analog, each of which has substantially the same or better potency than that of GLP-1.

15. The method of claim 11, wherein said GLP-1 compound is delivered continuously.

16. The method of claim 15, wherein the rate of delivery is equivalent to about 0.25 to 6 pmol/kg body weight/min, preferably from about 0.5 to about 1.2 pmol/kg/min, or from about 0.6 to about 2.4 pmol/kg/min of GLP-1.

17. The method of claim 15, wherein the entire delivery period for said GLP-1 compound is about 6 hrs, about 12 hrs, about 1 day, about 3 days, about 5 days, about 2 weeks, about 1 month, about 3 months, about 6 months, about 1 year or more.

18. The method of claim 11, wherein said GLP-1 compound is delivered intermittently.

19. The method of claim 18, wherein the rate of delivery, as averaged over the entire delivery period, is equivalent to about 0.25 to 6 pmol/kg body weight/min, preferably from about 0.5 to about 1.2 pmol/kg/min, or from about 0.6 to about 2.4 pmol/kg/min of GLP-1.

20. The method of claim 18, wherein the entire deliver period for said GLP-1 compound is about 6 hrs, about 12 hrs, about 1 day, about 3 days, about 5 days, about 2 weeks, about 1 month, about 3 months, about 6 months, about 1 year or more.

21. The method of claim 11, further comprising a needle functionally connected to the output orifice for delivery of GLP-1 compound expelled from said fluid storage chamber to an individual.

22. The method of claim 11, wherein said first actuator comprises two or more springs.

23. The method of claim 11, wherein said second actuator comprises two or more springs.

24. The method of claim 11, wherein the viscosity of said high viscosity fluid is about ISO VG 1500 or more.

25. The method of claim 11, wherein said first actuator causes constant delivery of said GLP-1 compound, and said second actuator causes a bolus delivery of said GLP-1 compound under patient control.

26. The method of claim 11, wherein said first actuator generates a force of from about 0.001 lbs to about 10 lbs.

* * * * *